US012102717B2

(12) United States Patent
Bozkurt et al.

(10) Patent No.: US 12,102,717 B2
(45) Date of Patent: *Oct. 1, 2024

(54) HOLLOW SILICA SPHERES WITH NESTED IRON OXIDE PARTICLES

(71) Applicant: Imam Abdulrahman Bin Faisal University, Dammam (SA)

(72) Inventors: Ayhan Bozkurt, Dammam (SA); Seyda Tugba Gunday Anil, Dammam (SA); Firdos Alam Khan, Dammam (SA); Sultan Akhtar, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/200,055

(22) Filed: May 22, 2023

(65) Prior Publication Data

US 2023/0301918 A1    Sep. 28, 2023

Related U.S. Application Data

(60) Continuation of application No. 17/823,750, filed on Aug. 31, 2022, which is a division of application No. 16/403,049, filed on May 3, 2019, now Pat. No. 11,491,110.

(51) Int. Cl.
| | | |
|---|---|---|
| *A61K 9/16* | (2006.01) | |
| *A61K 33/00* | (2006.01) | |
| *A61K 33/26* | (2006.01) | |
| *A61K 45/06* | (2006.01) | |
| *A61P 35/00* | (2006.01) | |

(52) U.S. Cl.
CPC .............. *A61K 9/16* (2013.01); *A61K 9/1682* (2013.01); *A61K 33/00* (2013.01); *A61K 33/26* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,945,525 A | 8/1999 | Uematsu | |
| 9,220,685 B2 | 12/2015 | Torgler et al. | |
| 11,242,256 B2* | 2/2022 | Bozkurt | .......... C01B 33/18 |
| 11,957,789 B2* | 4/2024 | Bozkurt | ............ A61K 9/0014 |
| 2016/0051471 A1* | 2/2016 | Haynes | .............. A61K 33/26 |
| | | | 424/94.1 |
| 2018/0065859 A1 | 3/2018 | Kummel et al. | |

FOREIGN PATENT DOCUMENTS

| | | |
|---|---|---|
| CN | 102786061 B | 1/2014 |
| CN | 102967706 B | 9/2014 |
| CN | 103919803 B | 7/2018 |
| KR | 10-0514600 | 9/2005 |

OTHER PUBLICATIONS

Wang et al.; "Mechanism of a self-templating synthesis of monodispersed hollow silica nanospheres with tunable size and shell thickness," 2007, RSC, Chemical Communications, vol. 23, pp. 2339-2341. (Year: 2007).*
Ansari et al.; "Improved anticancer efficacy of epirubicin by magnetic mesoporous silica nanoparticles: in vitro and in vivo studies," Apr. 24, 2018; Taylor & Francis; Artificial Cells, Nanomedicine, and Biotechnology vol. 46, No. S2, pp. S594-S606, and supporting information (21-pages total)(Year: 2018).*
Chen et al.; "Core/Shell Structured Hollow Mesoporous Nanocapsules: A Potential Platform for Simultaneous Cell Imaging and Anticancer Drug Delivery," 2010; ACS Nano, vol. 4, No. 10, pp. 6001-6013. (Year: 2010).*
Kobayashi et al.; "Synthesis of spherical submicron-sized magnetite/silica nanocomposite particles," 2008; Journal of sol-gel science and technology, vol. 45, No. 1, pp. 35-41. (Year: 2008).*
Akhtar et al.; "A novel approach to produce monodisperse hollow pure silica spheres," 2019 (first published Sep. 22, 2018), Elsevier; Journal of Saudi Chemical Society, vol. 23, pp. 477-485. (Year: 2018).*
Cheng, et al. ; Template-etching route to construct uniform rattle-type Fe O @SiO hollow microspheres as drug carrier ; Materials Science and Engineering:C vol. 71 ; pp. 829-835 ; Jun. 1, 2017 ; Abstract Only ; 2 Pages.
Shen, et al. ; The use of hollow mesoporous silica nanospheres to encapsulate bortezomib and improve efficacy for non-small cell lung cancer therapy ; Biomaterials xxx ; pp. 1-11 ; 2013 ; 11 Pages.
Wu et al.; "Titania coated magnetic mesoporous hollow silica microspheres: fabrication and application to selective enrichment of phosphopeptides," 2010; The Royal Society of Chemistry; Chem. Commun., vol. 46, pp. 9031-9033. (Year: 2010).
Zukal et al.; "Mesoporous silica with controlled porous structure and regular morphology," 1999; Elsevier; International Journal of Inorganic Materials, vol. 1, pp. 97-102. (Year: 1999).
Ansari et al.; "Improved anticancer efficacy of epirubicin by magnetic mesoporous silica nanoparticles: in vitro and in vivo studies," Apr. 24, 2018; Taylor & Francis; Artificial Cells, Nanomedicine, and Biotechnology vol. 46, No. S2, pp. S594-S606. (Year: 2018).
Chin; "Synthesis of Silica Hollow Nanomaterials for Biomedical Applications," Doctor of Philosophy Thesis of Lip Son Chin, Sep. 2014, pp. 1-170, as provided. (Year: 2014).
Jordan et al.; "Local moderate magnetically induced hyperthermia using an implant formed in situ in a mouse tumor model," 2009, International Journal of Hyperthermia, vol. 25, No. 3, pp. 229-239. (Year: 2009).

(Continued)

*Primary Examiner* — Tigabu Kassa
*Assistant Examiner* — Ivan A Greene
(74) *Attorney, Agent, or Firm* — Oblon, McClelland, Maier & Neustadt, L.L.P.

(57) ABSTRACT

The invention pertains to a method for treating a neoplasm, such as colorectal cancer, using hollow silica spheres ("HSS"). It also is directed to a method for making uncalcined HSS, calcined HSS from which phenyl groups have been removed, and HSS incorporating particles of $Fe_3O_4$, as well as compositions containing HSS.

10 Claims, 9 Drawing Sheets

(56) References Cited

OTHER PUBLICATIONS

"EMG Series—Water-based Ferrofluid Type: EMG 308" retrieved from <ferrofluid.ferrotec.com/products/ferrofluid-emg/water/emg-308/> on Jun. 16, 2021, pp. 1-2. (Year: 2021).
Jolivet et al.; "Iron oxide chemistry. From molecular clusters to extended solid networks," 2004, RSC; Chemical communications, vol. 5, pp. 481-483. (Year: 2004).
Lin et al.; "Modulation of the mRNA-binding protein HuR as novel reversal mechanism of epirubicin-triggered multidrug resistance in colorectal cancer cells," PLOS-ONE, vol. 12, No. 10, pp. 1-19. (Year: 2017).
Akhtar et al.; "A novel approach to produce monodisperse hollow pure silica spheres", Journal of Saudi Chemical Society, vol. 23, No. 4, pp. 477-485. (Year 2019).

\* cited by examiner

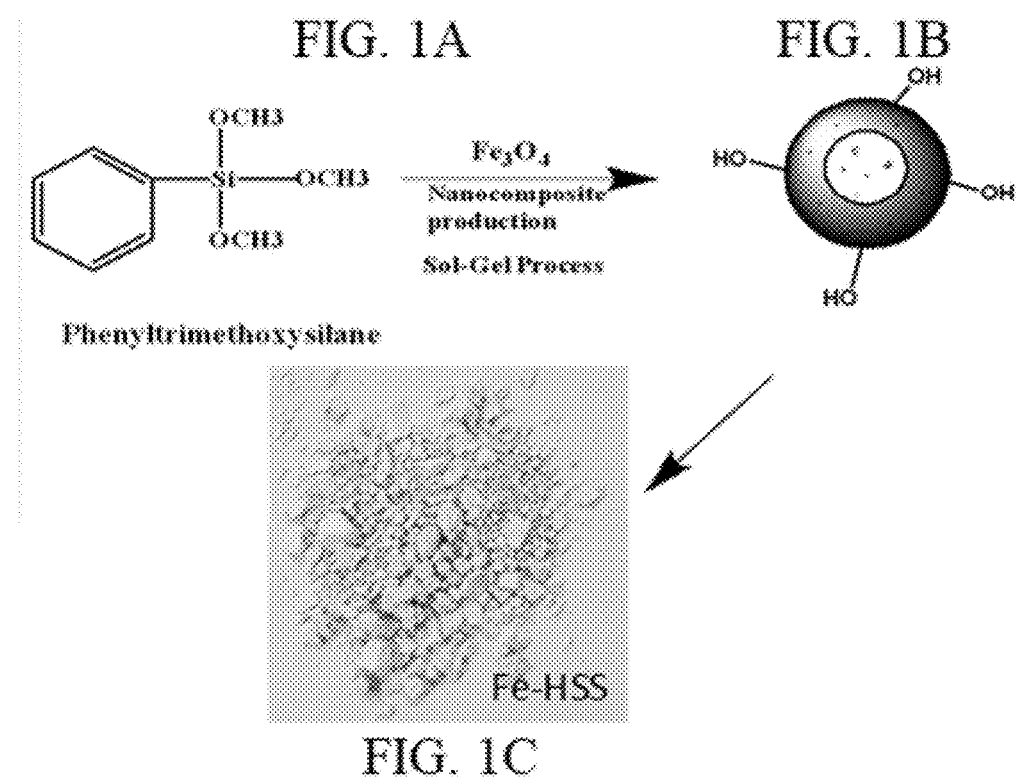

FIG. 5A  FIG. 5C  FIG. 5D
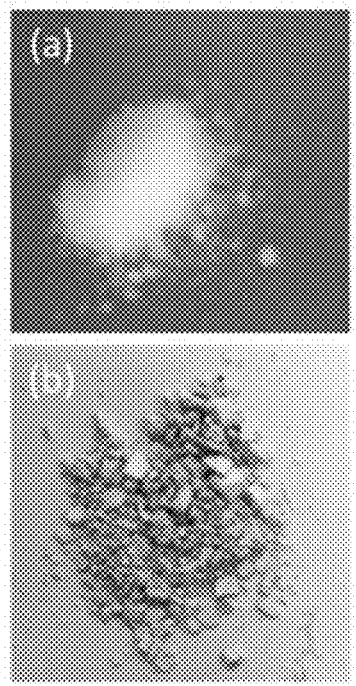
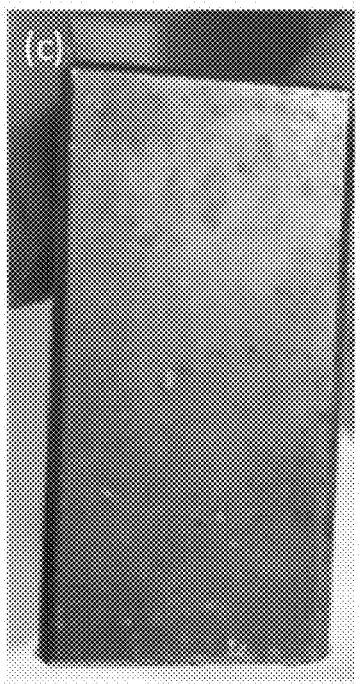
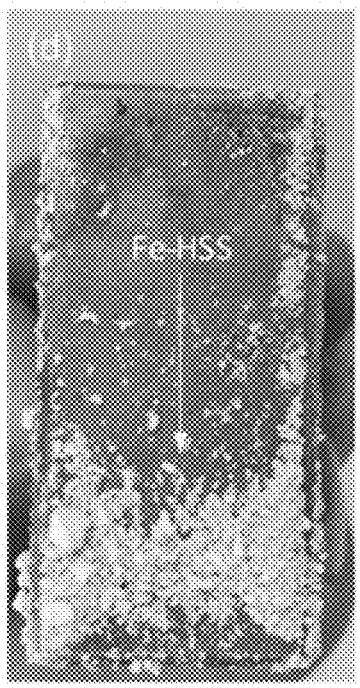
FIG. 5B
FIG. 6
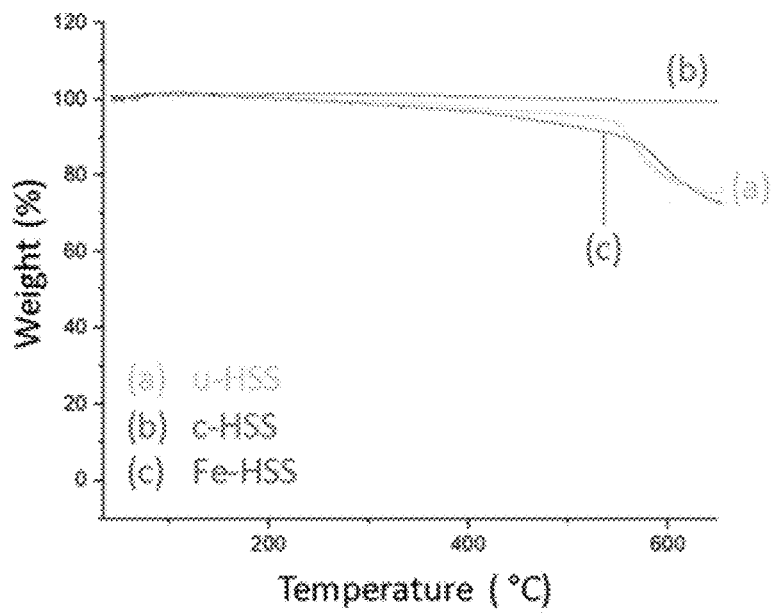

FIG. 7A 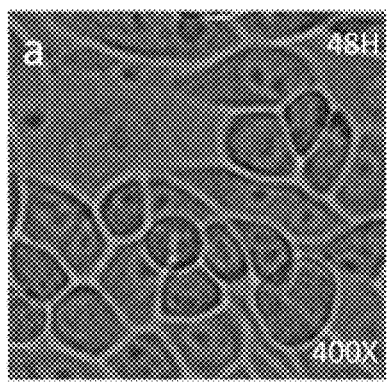 FIG. 7B 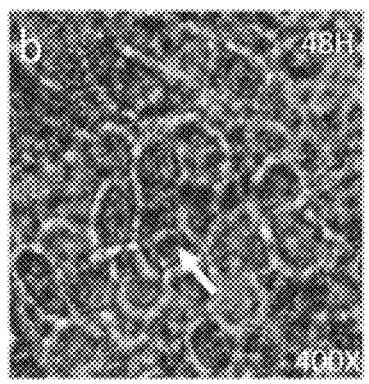 FIG. 7C 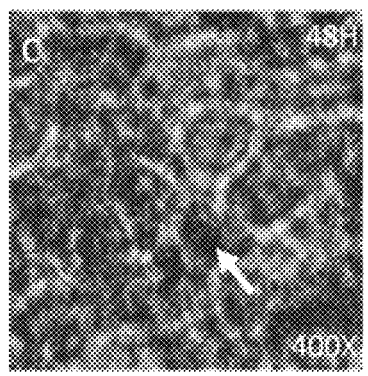
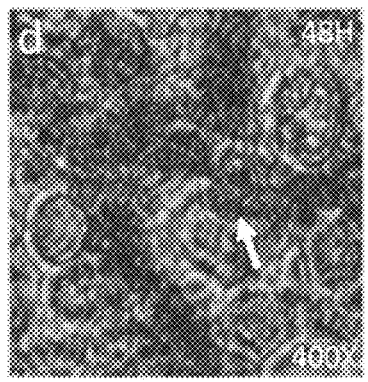 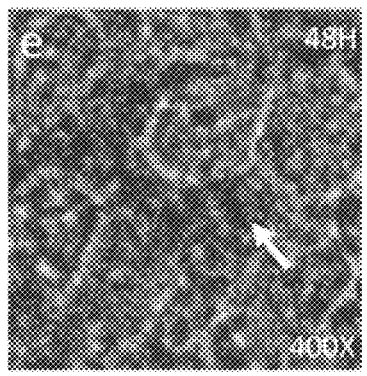
FIG. 7D  FIG. 7E FIG. 8A   FIG. 8B   FIG. 8C
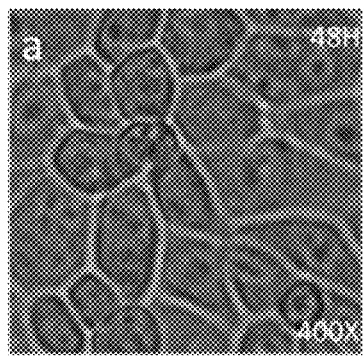 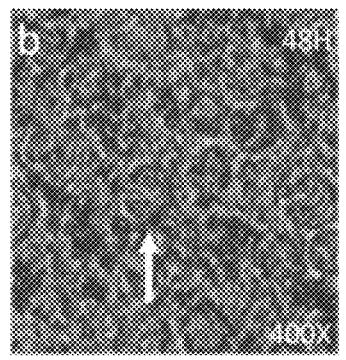 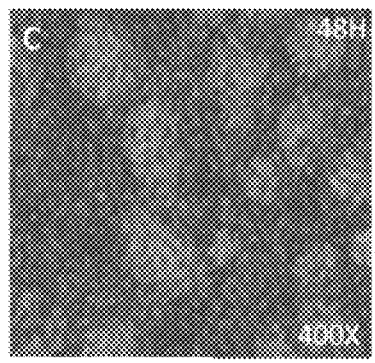
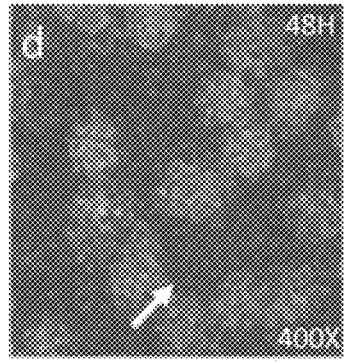 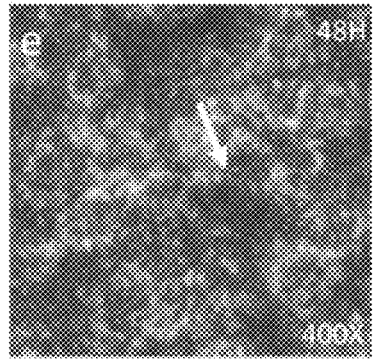
FIG. 8D   FIG. 8E

HOLLOW SILICA SPHERES WITH NESTED IRON OXIDE PARTICLES

CROSS-REFERENCE TO RELATED APPLICATION

The present application is a Continuation of U.S. application Ser. No. 17/823,750, pending, having a filing date of Aug. 31, 2022, which is a Divisional of U.S. application Ser. No. 16/403,049, now U.S. Pat. No. 11,491,110, having a filing date of May 3, 2019.

STATEMENT REGARDING PRIOR DISCLOSURES BY THE INVENTOR OR A JOINT INVENTOR

Related aspects of this technology are described by Akhtar, et al., J. Saudi Chemical Society (available online Sep. 22, 2018), which is incorporated by reference for all purposes.

BACKGROUND OF THE INVENTION

Field of the Invention

The invention pertains to the fields of medicine and biopolymer chemistry, especially to use of hollow silica spheres ("HSS") for treatment of neoplasms such as colorectal cancer.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Silica nanoparticles are used in many fields. They are used as scaffolds or carriers for chemical and biological materials, such as drugs or catalysts and also have been incorporated into lithium batteries, ceramics and sensors; Uysal, B. O., Tepehan, F. Z. Controlling the growth of particle size and size distribution of silica nanoparticles by the thin film structure. J. Sol-Gel Sci. Technol., 63 (1) (2012), pp. 177-18.

Silica nanoparticles are used to enhance the mechanical capabilities and increase the strength of thin films including anticorrosion films and superhydrophobic films; Ramezani, M., M. R. Vaezi, A. Kazemzadeh, Preparation of silane-functionalized silica films via two-step dip coating sol-gel and evaluation of their superhydrophobic properties. Appl. Surf. Sci., 317 (2014), pp. 147-153; Akhtar, S., et al. Enhancement of anticorrosion property of 304 stainless steel using silane coatings. Appl. Surf. Sci., 440 (2018), pp. 1286-1297.

Hollow silica spheres (HSS) having dimensions in the nanometer to micrometer ranges have emerged as a versatile material for many industrial, medical and scientific applications, including both therapeutic and diagnostic application. These include their use in drug delivery or biomolecular release systems and as imaging agents for medical diagnostics; Adhikari, C., et al. Drug delivery system composed of mesoporous silica and hollow mesoporous silica nanospheres for chemotherapeutic drug delivery. J. Drug Delivery Sci. Technol., 45 (2018), pp. 303-314; Rosu, C., et al. Polypeptide-coated silica particles dispersed in lyotropic liquid crystals of the same polypeptide. J. Phys. Chem. B, 120 (29) (2016), pp. 7275-7288; Jiang, Y., D. Mu, S. Chen, B. Wu, Z. Zhao, Y. Wu, Z. Ding, F. Wu. Hollow silica spheres with facile carbon modification as an anode material for lithium-ion batteries. J. Alloy Compd., 744 (2018), pp. 7-14; Jang J Y, Duong H T T, Lee S M, Kim H J, Ko Y J, Jeong J H, Lee D S, Thambi T, Son S U. Folate decorated hollow spheres of microporous organic networks as drug delivery materials. Chem Commun (Camb). 2018 Apr. 5; 54(29):3652-3655. doi: 10.1039/c8cc01240g; Yang Y, Lu Y, Abbaraju P L, Zhang J, Zhang M, Xiang G, Yu C. Multi-shelled Dendritic Mesoporous Organosilica Hollow Spheres: Roles of Composition and Architecture in Cancer Immunotherapy. Angew Chem Int Ed Engl. 2017 Jul. 10; 56(29):8446-8450. doi: 10.1002/anie.201701550. Epub 2017 May 3; Lv R, Zhong C, Gulzar A, Gai S, He F, Gu R, Zhang S, Yang G, Yang P. Synthesis, luminescence, and anti-tumor properties of $MgSiO_3$:Eu-DOX-DPP-RGD hollow microspheres. Dalton Trans. 2015 Nov. 14; 44(42): 18585-95. doi: 10.1039/c5dt03604f. Epub 2015 Oct. 8; Yang D, Yang G, Wang X, Lv R, Gai S, He F, Gulzar A, Yang P. $Y2O3$:Yb,Er@$mSiO_2$—Cu(x)S double-shelled hollow spheres for enhanced chemo-/photothermal-anti-cancer therapy and dual-modal imaging. Nanoscale. 2015 Jul. 28; 7(28):12180-91. doi: 10.1039/c5nr02269j. Epub 2015 Jul. 1; Teng Z, Su X, Zheng Y, Zhang J, Liu Y, Wang S, Wu J, Chen G, Wang J, Zhao D, Lu G. A Facile Multi-interface Transformation Approach to Monodisperse Multiple-Shelled Periodic Mesoporous Organosilica Hollow Spheres. J Am Chem Soc. 2015 Jun. 24; 137(24):7935-44. doi: 10.1021/jacs.5b05369. Epub 2015 Jun. 11; She X, Chen L, Velleman L, Li C, Zhu H, He C, Wang T, Shigdar S, Duan W, Kong L. Fabrication of high specificity hollow mesoporous silica nanoparticles assisted by Eudragit for targeted drug delivery. J Colloid Interface Sci. 2015 May 1; 445:151-160. doi: 10.1016/j.jcis.2014.12.053. Epub 2014 Dec. 25; Mohapatra S, Rout S R, Narayan R, Maiti T K. Multifunctional mesoporous hollow silica nanocapsules for targeted co-delivery of cisplatin-pemetrexed and MR imaging. Dalton Trans. 2014 Nov. 14; 43(42):15841-50. doi: 10.1039/c4dt02144d; Chang F P, Hung Y, Chang J H, Lin C H, Mou C Y. Enzyme encapsulated hollow silica nanospheres for intracellular biocatalysis. ACS Appl Mater Interfaces. 2014 May 14; 6(9): 6883-90. doi: 10.1021/am500701c. Epub 2014 Apr. 15; Chen Y, Chen H R, Shi J L. Construction of homogenous/heterogeneous hollow mesoporous silica nanostructures by silica-etching chemistry: principles, synthesis, and applications. Acc Chem Res. 2014 Jan. 21; 47(1):125-37. doi: 10.1021/ar400091e. Epub 2013 Aug. 14.

Despite the many benefits of hollow silica spheres they are have not been successful as agents for cancer therapy. The inventors believe that this is accounted for by the presence of phenyl groups which may impair or prevent the HSS from exhibiting pharmacokinetic and pharmacodynamics properties useful for treating cancer and other neoplasms. HSS bearing phenyl groups are resistant to degradation in the body due to the inability or relatively poor ability (compared to HSS without phenyl groups) of the body to metabolize phenyl groups through the liver and bile and thus be easily cleared from the body. HSS that remain in the body pose significant safety and health hazards, for example due to the presence of the phenyl groups which may form be released as benzene.

The inventors have overcome the problem associated with the presence of phenyl groups and show that HSS without phenyl groups and/or HSS which incorporate $Fe_3O_4$ particles, surprisingly exhibit superior anti-cancer properties.

Accordingly, it is one object of the present invention to provide a method to synthesize HSS and efficiently remove non-degradable phenyl groups and to produce hollow silica spheres containing $Fe_3O_4$ and the hollow nanoparticles obtained therefore. Unlike many prior processes of making HSS, this method does not require the use of template.

BRIEF SUMMARY OF THE INVENTION

The invention pertains to a method for treating a neoplasm, such as colorectal cancer, using hollow silica spheres ("HSS"). It also is directed to a method for making uncalcined HSS, calcined HSS from which phenyl groups have been removed, and HSS incorporating particles of $Fe_3O_4$, as well as compositions containing HSS.

The following non-limited embodiments discloses particular aspects of this technology.

According to a first aspect of the invention, the present disclosure relates to a method for treating a subject having a neoplasm comprising contacting a neoplastic cell with hollow silica spheres ("HSS") selected from the group consisting of at least one of an uncalcined hollow silica sphere ("u-HSS"), a calcined hollow silica sphere ("c-HSS") or a $Fe_3O_4$-hollow silica sphere ("Fe—HSS"), wherein said hollow silica spheres are substantially free of phenyl groups.

In some embodiments of this method, the hollow silica spheres are prepared by a process comprising hydrolysis of phenyl-tri-methoxysilane ("PTMS") or another hydrolyzable aryl silane followed by condensation with a hydroxide base.

In some embodiments of the invention the HSS are u-HSS, c-HSS and/or Fe-HSS.

In some embodiments the HSS further comprise at least one anticancer drug or agent.

In some embodiments, the neoplasm is cancer.

In some embodiments, the neoplasm is colon or colorectal cancer.

In some embodiments, the neoplasm is at least one of non-melanoma skin cancer, breast cancer, lung cancer, prostate cancer, melanoma, bladder cancer, non-Hodgkin's lymphoma, kidney cancer, leukemia, pancreatic cancer, thyroid cancer, liver cancer, endometrial cancer, throat cancer, ovarian cancer, or testicular cancer.

In some embodiments the neoplasm is a benign neoplasm.

In some embodiments the neoplasm is a pre-cancerous tumor or precancerous lesion.

In some embodiments, the HSS are administered in situ to the site of a tumor or cancer cells.

In some embodiments, the HSS are administered parenterally.

In some embodiments, the HSS are administered subcutaneously, intramuscularly, or intravenously.

In some embodiments, the HSS are administered tropically.

In some embodiments, the HSS are administered orally.

In some embodiments an amount of HSS is administered sufficient to disrupt the nuclear membrane of a neoplastic cell for example by inducing nuclear condensation, augmentation, and/or disintegration/fragmentation. In other embodiments, an amount of HSS is administered sufficient to disrupt the cellular membrane of a cancer cell.

Another aspect of the invention is directed to a composition comprising hollow silica spheres ("HSS") selected from the group consisting of at least one of an uncalcined hollow silica sphere ("u-HSS"), a calcined hollow silica sphere ("c-HSS") or a $Fe_3O_4$-hollow silica sphere ("Fe-HSS"). Preferably, the hollow silica spheres are substantially free of phenyl or other aryl groups, for example, c-HSS may contain <0.01, 0.02, 0.05, 0.1, 0.2, 0.5, 1, 2, 5, 10, 20, or 50 molar % of the phenyl or aryl groups present on corresponding uncalcined HSS such as the u-HSS disclosed herein. All phenyl groups on the surface and in the core can be removed via calcination and this can be confirmed by TGA and FT-IR. For example, uncalcined Fe-HSS may be calcined to remove all or a portion of the phenyl groups and/or to reduce the size of the calcined Fe-HSS compared to uncalcined Fe-HSS. Calcined HSS are typically smaller that the corresponding u-HSS, for example, they may be 5, 10, 15, 20, 25, 30, 35, 40, 45 or 50% smaller in average diameter than corresponding u-HSS.

In some embodiments, the u-HSS have an average diameter ranging from 660, 710, 760, 810, to 860 nm or any intermediate value within this range.

In some embodiments the c-HSS and Fe-HSS have average diameters ranging from 415, 465, 515, 565 to 615 nm or any intermediate value within this range.

In some embodiments Fe-HSS will contain about <0.05, 0.05, 0.1, 0.2, 0.5, 1, 2, 5, 10, to >10 wt % $Fe_3O_4$ particles based on the total weight of the Fe-HSS (e.g., the weight of the $Fe_3O_4$ particles+the weight of the HSS). These particles may consist of, consist essentially of, or comprise $Fe_3O_4$. In some embodiments, other types of magnetic materials may be substituted in whole or part for $Fe_3O_4$, these other materials include corresponding Ni or Co compounds such as NiO or $Co_3O_4$ based on total weight of the Fe-HSS. In other embodiments either superparamagnetic iron oxide particles with a mean hydrodynamic diameter of >50 nm such as feruxomides or Feridex IV may be used. In still other embodiments ultra small superparamagnetic iron oxide particles with a hydrodynamic diameter of <50 nm such as Ferumoxtran-10 may be incorporated into HSS. In some embodiments, the silica-containing shell of the HSS is thicker than its core and in other embodiments, the core is thicker than the shell.

In some embodiments, the silica-containing shell has a thickness of about 150, 160, 170, 180, 190, 200 to 210 nm or any intermediate value within this range, and the core has a diameter of about 100, 110, 120, 130, 140, 150, 160, 170, 180, 190, 200, 210, 220 to 230 nm or any intermediate value within this range.

In some embodiments the HSS is Fe-HSS that comprises $Fe_3O_4$ particles having an average diameter ranging from 9.5, 10, 11, 12, 13, 14, 15, 16, 17, 18, 19, 20, 21 to 21.3 nm or any intermediate value within this range.

In some embodiments, the hollow silica spheres are monodisperse with a coefficient of variation, defined as a ratio of the standard deviation to the mean diameter of the hollow silica spheres, of less than 1, 2, 3, 4 or 5%.

In some embodiments, the hollow silica spheres have a solubility in water of 0.1, 0.2, 0.5, 1, 1.2, 1.5, 2, 5, 10, 20, to 50 mg per 10 mL of water or any intermediate value within this range.

In some embodiments, the hollow silica spheres have a specific surface area of 350, 360, 370, 380, 390, 400, 410, 420, 430, 440 to 450 $m^2/g$ or any intermediate value within this range.

In some embodiments, the hollow silica spheres have a t-plot external surface area of 40, 45, 50, 55, 60, 65, 670 to 75 $m^2/g$ or any intermediate value within this range.

In some embodiments, the hollow silica spheres have an average pore diameter of 1.7 to 8 nm with a cumulative pore volume of 0.02, 0.025, 0.03, to 0.035 $cm^3/g$ or any intermediate value within this range.

In some embodiments, the HSS further comprise at least one anticancer drug or agent.

In some embodiments, the HSS further comprise a coating such as a cationic polymer such as chitosan.

In some embodiments, the HSS further comprise a targeting agent, such as a tumor-specific antibody or antibody fragment such as Fab or Fab2 or another ligand that binds to neoplastic, cancer or tumor cells.

Another aspect of the invention sis directed to a method for forming hollow silica spheres ("HSS") comprising: dissolving a hydrolyzable aryl silane in an aqueous solution comprising water and an acid to form a hydrolyzed silane solution; mixing the hydrolyzed silane solution with a hydroxide base to form a precipitate; and recovering hollow silica spheres from the precipitate.

In some embodiments of this method the hydrolyzable aryl silane is trimethoxy(phenyl) silane.

In some embodiments of this method the hydroxide base is $NH_4OH$.

In some embodiments, this method further comprises calcining the silica spheres at a temperature that removes phenyl groups from uncalcined HSS, thereby forming c-HSS.

In some embodiments, the method further comprises incorporating $Fe_3O_4$ into the aqueous solution containing the hydrolyzable aryl silane, and adding the hydroxide base, thereby forming Fe-HSS.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIGS. 1A-1C: Substrates and sol-gel process (FIG. 1A) used to prepare $Fe_3O_4$ nanoparticles incorporated hollow silica spheres or Fe-HSS (FIG. 1B). A photo of the prepared product is shown in FIG. 1C.

(FIG. 2A) TEM image and (FIG. 2B) size histogram of $Fe_3O_4$ particles. The average diameter of the particles is ~14 nm. (FIG. 2C) SAED pattern of the $Fe_3O_4$ nanoparticles, showing the polycrystalline nature, the first 5-rings of the pattern started from the inner ring are indexed as, (220), (311), (400), (511) and (440). SEM micrograph of (FIG. 2D) u-HSS, (FIG. 2E) c-HSS and (FIG. 2F) Fe-HSS.

FIGS. 5A-5D. A digital photograph of physical appearance of (FIG. 5A) c-HSS and (FIG. 5B). A digital photograph of the magnetic slab to attract the $Fe_3O_4$ powder (FIG. 5C) before and (FIG. 5D) after performing the test. The Fe-HSS powder can be seen attached to the magnetic slab.

FIG. 6. TGA plots of the u-HSS (a) orange plot, c-HSS (a) red plot, and Fe-HSS (c) blue plot.

FIGS. 7A-7E. Morphology of cancer cells morphology after treatment of Uncal-HSS: The HCT-116 cells analyzed 48 hrs post-treatments. FIG.s showed the effects of HSS-1, (FIG. 7A) control, (FIG. 7B) treated with dose 2 ul/0.1 ml, (FIG. 7C) treated with 4 ul/0.1 ml, (FIG. 7D) treated with 6 ul/0.1 ml and (FIG. 7E) treated with 8 ul/0.1 mL. Arrows show cellular disintegration of cancer cells. 400× magnifications FIGS. 8A-8E. Morphology of cancer cells morphology after treatment of Cal-HSS: The HCT-116 cells analyzed 48 hrs post-treatments. FIG.s showed the effects of HSS-2, (FIG. 8A) control, (FIG. 8B) treated with dose 2 ul/0.1 ml, (FIG. 8C) treated with 4 ul/0.1 ml, (FIG. 8D) treated with 6 ul/0.1 ml and (FIG. 8E) treated with 8 ul/0.1 mL. Arrows show cellular disintegration of cancer cells. 400× magnifications FIGS. 9A-9E. Morphology of cancer cells morphology after treatment of Fe-HSS: The HCT-116 cells analyzed 48 hrs post-treatments. FIGS. showed the effects of HSS-3, (FIG. 9A) control, (FIG. 9B) treated with dose 2 ul/0.1 ml, (FIG. 9C) treated with 4 ul/0.1 ml, (FIG. 9D) treated with 6 ul/0.1 ml and (FIG. 9E) treated with 8 ul/0.1 mL. Arrows show cancer cell nuclear augmentation and condensation.

DETAILED DESCRIPTION OF THE INVENTION

Figure 2A:
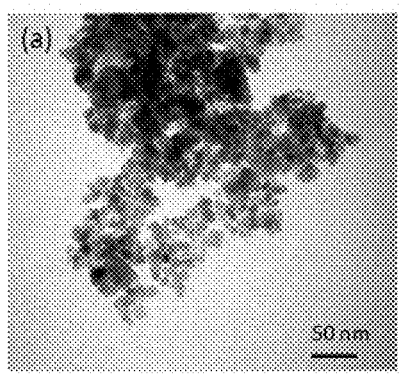
FIGS. 2A-2F. Morphology and size analysis of the $Fe_3O_4$ nanoparticles and hollow silica spheres (HSS).

As explained above the inventors have now synthesized and compared uncalcined-hollow silica spheres (u-HSS), calcined hollow silica spheres (c-HSS) and $Fe_3O_4$-hollow silica spheres (Fe-HSS). Calcination was used to remove phenyl groups. Further detail about the substrates for HSS and the steps of producing and analyzing anti-cancer properties of HSS are provided below.

Silica Spheres. When referencing hollow silica spheres, "hollow" refers to a central area (i.e., a core portion) of a particle which has a lower density of silica compared to the surrounding structure (i.e., the shell portion). While the definition of "hollow" may encompass a continuous void that is completely free of silica, this is not a requirement, and some silica may be disposed within the core portion. By way of example, a silica particle which has a substantially continuous density of silica from one point on the particle though the center of the particle to a point directly across from it would be considered solid herein and not hollow, whereas a silica particle that has 60-80 wt. % of a total silica content located in the shell portion, with the remaining 20-40 wt. % of a total silica content located in the central area would be considered hollow herein.

The "degree of hollowness" of the hollow silica spheres as used herein is an indicator of the density differential between the silica-containing shell and the core, with higher degrees of hollowness being associated with an increased capacity for storage (e.g., of pharmaceutical or cosmetic payloads), adsorption, etc. The degree of hollowness is defined as a maximum peak intensity of the core divided by a minimum peak intensity of the silica-containing shell, each of which are measured by transmission electron microscopy. That is, given the higher density of silica in the silica-containing shell than in the core, it is more difficult for a beam of electrons to pass through the silica-containing shell, resulting in intensity profiles that can be used to quantify this silica density disparity. The degrees of hollowness can then be calculated for the individual hollow silica spheres and averaged. In some embodiments, the hollow silica spheres produced herein have an average degree of hollowness of 3, 4, 5, 6, 7 to 8, preferably 3.2 to 7.5, preferably 3.4 to 7.0, preferably 3.6 to 6.5, preferably 3.8 to 6.0, preferably 4.0 to 5.5, preferably about 4.06. Such a degree in hollowness is much higher (i.e., more hollow) than silica spheres which have not been calcined, which have an average degree of hollowness of about 2.3.

HSS Shape. The shape of the core may generally determine the shape of the hollow silica spheres. In a preferred embodiment, the hollow silica spheres are spherical or substantially spherical. Sphericity is a measure of how closely the shape approaches that of a mathematically perfect sphere, and is defined as the ratio of the surface area of a perfect sphere having the same volume as a hollow silica sphere to the surface area of the hollow silica sphere (with unity being a perfect sphere). Preferably the hollow silica spheres have a high sphericity, with an average sphericity of at least 0.9, preferably at least 0.92, preferably at least 0.94, preferably at least 0.96, preferably at least 0.98, preferably at least 0.99. In some embodiments, the hollow silica spheres are classified based on roundness, and are categorized herein as being sub-rounded, rounded, or well-rounded, preferably well-rounded, using visual inspection similar to characterization used in the Shepard and Young comparison chart.

It is also envisaged that hollow silica particles may be manufactured in shapes other than spheres having high sphericities and roundness as described above. By way of example, particles may be produced in shapes such as rods, cylinders, rectangles, triangles, pentagons, hexagons, prisms, disks, platelets, cubes, cuboids, flakes, stars, flowers, and urchins (e.g. a globular particle possessing a spiky uneven surface).

In preferred embodiments, the methods disclosed herein produce hollow silica spheres which are uniform. As used herein, the term "uniform" refers to no more than 10%, preferably no more than 5%, preferably no more than 4%, preferably no more than 3%, preferably no more than 2%, preferably no more than 1% of the distribution of the hollow silica spheres having a different shape. For example, the hollow silica spheres are highly spherical (e.g., have an average sphericity of at least 0.9) and have no more than 1% of nanocomposite hollow particles in an oblong shape. Included in this definition of "uniform" is the degree in which the hollow silica spheres remain intact. In preferred embodiments, the silica-containing shell completely surrounds the hollow core, so that no fluid or compound may ingress into or egress out of the core except through pores located within the silica-containing shell. However, when a sphere is ruptured slightly so that silica-containing shell does not completely surround the core, the ruptured sphere tends to take on an appearance of a deflated, dimpled, or crumpled sphere, and thus tends to have a lowered sphericity (e.g., below that of 0.9). Similarly, when a significant rupture occurs, the spherical particles may take on the form of angular shards or fragments which have a substantially different shape than highly spherical particles. Therefore, uniformity may also be used to measure the mechanical resistance to rupture, with adequate uniformity (e.g., no more 10% of particles having a varied shape) being an indicator for high mechanical strength of the produced hollow silica spheres.

In some embodiments, the silica-containing shell has a thickness of about 150 to 210 nm, preferably 160 to 200 nm, preferably 170 to 190 nm, preferably 180 to 185 nm. In some embodiments, the core has a diameter of about 100 to 230 nm, preferably 110 to 220 nm, preferably 120 to 210 nm, preferably 130 to 200 nm, preferably 140 to 190 nm, preferably 150 to 180 nm, preferably 160 to 170 nm. In preferred embodiments, the silica-containing shell is of "uniform thickness", meaning an average shell thickness that differs by no more than 10%, no more than 8%, no more than 6%, no more than 4%, preferably no more than 2%, preferably no more than 1% at any given location on the silica-containing shell.

In some embodiments, the methods herein produce hollow silica spheres with an average diameter of 490 to 540 nm, preferably 500 to 530 nm, preferably 505 to 525, preferably 510 to 520, with the diameter being the longest linear distance measured from one point on the particle though the center of the particle to a point directly across from it. Instead, when no calcination procedure is performed, the non-calcined silica spheres have much larger particle sizes, with an average diameter of about 760 nm.

"Dispersity" is a measure of the homogeneity/heterogeneity of sizes of particles in a mixture. The coefficient of variation (CV), also known as relative standard deviation (RSD) is a standardized measure of dispersion of a probability distribution. It is expressed as a percentage and may be defined as the ratio of the standard deviation ($\sigma$) to the mean ($\mu$, or its absolute value $|\mu|$), and it may be used to show the extent of variability in relation to the mean of a population. In a preferred embodiment, the hollow silica spheres of the present disclosure have a narrow size dispersion, i.e., are monodisperse, with a coefficient of variation of less than 30%, preferably less than 25%, preferably less than 20%, preferably less than 15%, preferably less than 12%, preferably less than 10%, preferably less than 8%, preferably less than 5%, preferably less than 3%, with the coefficient of variation being defined in this context as the ratio of the standard deviation to the mean diameter of the hollow silica spheres.

In some embodiments, the hollow silica spheres produced by the methods herein are in the form of distinct particles which are not present as agglomerates, meaning the hollow silica spheres are well-separated from one another and do not form clusters. On the other hand, non-calcined silica spheres are typically interconnected forming agglomerates made of two or more spheres that share an outer silica boundary.

The methods of the present disclosure advantageously produce hollow silica spheres having surface characteristics and porosities that make them suitable for use in a variety of applications, for example delivery, adsorption, biosensor, catalysis, and/or cosmetic applications. Such surface characteristics (e.g., specific surface area, Langmuir surface area, t-pot external surface area, etc.) and porosities (e.g., pore diameters, pore volume, etc.) can be measured, for example, using a gas sorption instrument such as a Micrometrics ASAP 2020 plus system (Micrometrics, USA). In some embodiments, the hollow silica spheres are produced with a specific surface area (BET surface area or multilayer adsorption) in the range of 350 to 450 $m^2/g$, preferably 360-440 $m^2/g$, preferably 370-430 $m^2/g$, preferably 380-420 $m^2/g$, preferably 390-415 $m^2/g$, preferably 400-410 $m^2/g$, preferably 405-408 $m^2/g$, preferably about 406 $m^2/g$. The specific surface area of the as produced hollow silica spheres is greater than the specific surface area of the non-calcined silica spheres, which is about 4-5 $m^2/g$.

In some embodiments, the hollow silica spheres have a Langmuir surface area (monolayer adsorption) of 550 to 700 $m^2/g$, preferably 560-690 $m^2/g$, preferably 570-680 $m^2/g$, preferably 580-670 $m^2/g$, preferably 590-660 $m^2/g$, preferably 600-650 $m^2/g$, preferably 610-640 $m^2/g$, preferably about 635 $m^2/g$. The Langmuir surface area of the hollow silica spheres produced with the inventive methods is therefore greater than the Langmuir surface area of the non-calcined silica spheres, which is about 7.5-8.5 $m^2/g$.

The t-plot method is a well-known technique which allows determining the external micro- and/or mesoporous volumes and the specific surface area of a sample by comparison with a reference adsorption isotherm of a non-porous material having the same surface chemistry. In some embodiments, the hollow silica spheres have a t-plot external surface area of 40 to 75 $m^2/g$, preferably 45 to 70 $m^2/g$, preferably 50 to 65 $m^2/g$, preferably 55 to 60 $m^2/g$, preferably about 58 $m^2/g$. On the other hand, non-calcined silica spheres have a t-plot external surface area of 5-6 $m^2/g$.

In preferred embodiments, the hollow silica spheres of the present disclosure have an average pore diameter of 1.7 to 8 nm, preferably 2.0 to 6 nm, preferably 2.1 to 4 nm, preferably about 2.2 nm, and a BJH adsorption cumulative pore volume (of pores between 1.7 nm and 300 nm) of 0.02 to 0.035 $cm^3/g$, preferably 0.024 to 0.030 $cm^3/g$, preferably 0.026 to 0.028 $cm^3/g$, or about 0.027 $cm^3/g$. In contrast, the average pore diameter and the BJH adsorption cumulative pore volume (of pores between 1.7 nm and 300 nm) for silica spheres which have not been calcined are 10-11 nm and 0.016-0.017 $cm^3/g$, respectively.

The methods disclosed herein also form robust hollow silica spheres having desirable mechanical strength that resist rupture when placed under certain stresses. One way to test the mechanical strength is to subject the hollow silica spheres to ultrasonication for 5-10 min at a frequency of 5-30 kHz, preferably 10-25 kHz, preferably 15-20 kHz, and with a power intensity of 25-50 $W/cm^2$, preferably 30-45 $W/cm^2$, preferably 35-40 $W/cm^2$ at 20-25° C. A comparison between the number of broken/ruptured hollow silica spheres before and after the sonication using visual inspection, for example with SEM or TEM images, then provides a measure of mechanical strength, in terms of the percent remaining highly spherical (e.g., having an average sphericity of at least 0.9). In some embodiments, the hollow silica spheres produced by the methods of the present disclosure remain uniform after subjecting to ultrasonication. That is, no more than 10%, preferably no more than 5%, preferably no more than 1% of the distribution of the hollow silica spheres rupture (have a sphericity of less than 0.9) upon prolonged exposure to ultrasonication. This contrasts to most hollow silica spheres produced by template methods, which tend to crater or rupture easily under mechanical stress and thus have the tendency to be non-uniform, i.e., greater than 10% of a population having a different shape (Liu et al. "Preparation of hollow silica spheres with different mesostructures" Journal of Non-Crystalline Solids, 2008, 354, 826-830; Gorsd et al. "Synthesis and Characterization of Hollow Silica Spheres", Procedia Materials Science, 2015, 8, 567-576).

The methods disclosed herein also advantageously produce hollow silica spheres which have at least marginal solubility in water and thus can be used more readily in aqueous-based applications, such as in vivo drug delivery. In some embodiments, the hollow silica spheres have a solubility in water at ambient conditions of 0.1 to 50 mg per 10 mL of water, preferably 0.2 to 45 mg per 10 mL of water, preferably 0.5 to 40 mg per 10 mL of water, preferably 1 to 35 mg per 10 mL of water, preferably 2 to 30 mg per 10 mL of water, preferably 3 to 25 mg per 10 mL of water, preferably 5 to 20 mg per 10 mL of water, preferably 10 to 15 mg per 10 mL of water. Conversely, silica spheres which have not been calcined using the procedures described herein, have limited or no solubility in water under ambient conditions with solubilities less than 0.1 mg per 10 mL of water, preferably less than 0.01 mg per 10 mL of water, preferably less than 0.001 mg per 10 mL of water, preferably 0 mg per 10 mL of water. Such low or no aqueous solubility may prohibit the use of non-calcined silica spheres in certain applications such as drug delivery without performing surface modification steps to aid the aqueous solubility, which of course comes at the expense of time, scalability, material throughput, and production cost.

While phenyl and other aryl groups may be removed by single or multistep calcining, the use of particular multi-staged calcining steps provides a benefit. From the above description it is clear that the methods, which most notably involve use of a hydrolyzable aryl silane and a multi-stage calcining procedure, provide hollow silica spheres having superior uniformity, degrees of hollowness, mechanical properties, aqueous solubility, surface characteristics, etc. compared to non-calcined variants. Further, the inventors have unexpectedly discovered that particular multi-stage calcining procedures surprisingly provide hollow silica spheres with superior sphericity, degree of hollowness, uniformity, and/or monodispersity, compared to otherwise identical processes using different calcining programs, for example methods employing single-stage calcining procedures. By way of example, when a single-stage calcination procedure (that is, one that involves ramping from one temperature to another at a particular rate without any intermediate holding steps) is employed that involves calcining the precipitate by heating up to 600° C. at a ramp rate of 10° C./min, the resulting product has a low sphericity (e.g., less than 0.9), is not uniform (e.g. more than 10% of the distribution have a different shape), is not substantially hollow (e.g., has a degree of hollowness of less than 2), and has a low monodispersity (has a particle size coefficient of variation of greater than 30%).

This is surprising since the ramping rate and final calcining temperature of the single-stage calcination program are similar to those employed in the multi-stage calcining program of the present disclosure. Without being bound by theory, the superior and unexpected results demonstrated may be because the multi-stage (e.g., two-stage) calcination program provides sufficient time for the aryl groups of the hydrolyzable aryl silane to sequester and orient themselves within the center of the spherical particles, while the silanol functionality aggregate to face the surroundings, akin to the packing behavior of oil-in-water micelles. Therefore, the step-wise temperature increase of the multi-stage program may advantageously allow for reorientation of the hydrophobic and hydrophilic groups while the aryl groups are ultimately being removed through the increasing temperature, thereby forming the hollow core and providing the hollow silica spheres with the aforementioned properties without the need for templates.

The above described advantages enable the hollow silica spheres to be useful in many applications, including drug delivery/carrier applications, biosensors, catalysis, cosmetics, adsorbent applications, fillers in polymer, building, or construction applications, and the like.

In particular, the aqueous solubility properties of the hollow silica spheres allows them to be used directly as a carrier for sustained release of antitumor agents. For example, the hollow silica spheres may be loaded with one or more antitumor agents such as adriamycin, taxol, docetaxel, vincristine sulfate, fluorouracil, methotrexatum, novantrone, cyclic adenosine monophosphate, cyclophosphamide, peplomycin sulfate, nitrocaphane, solazigune, aclarubicin hydrochloride, carmustine, temozolomide, lomustine, carmofur, tegafur, dactinomycin, mitomycin, amsacrine, amifostine, cisplatin, alarelin, aminoglute-thimide, chlormethine hydrochloride, and the like, including derivatives thereof, for combating various types of cancers, including, but not limited to, lung cancer, breast cancer, melanoma, colon cancer, pancreatic cancer, glioma, hepatic tumors, pulmonary tumors, bone tumors, adrenal tumors and other solid tumors. The mode of delivery is not limited and may involve targeted or non-targeted delivery, for example through combination with a targeting agent such as tumor specific folic acid ligand or a tumor specific antibody.

Further, due to the sphericity, degree of hollowness, high surface areas, and porosity, the products formed from the methods disclosed herein are result in small pressure drops, making them especially suitable for adsorptive applications for processing of gases, vapors, liquids and solutions. Accordingly, the hollow silica spheres are useful for various chromatographic applications.

Substrates for HSS. The hydrolyzable aryl silane employed may be any silane having at least one aryl substituent and at least one hydrolyzable group bonded directly to the Si atom. Hydrolyzable groups include, but are not limited to, alkoxy groups (e.g., methoxy, ethoxy, propoxy, iso-propoxy, t-butoxy, as well as substituted variants, as well as mixtures of one or more of these groups) and halo groups (e.g., chloro, bromo, iodo, and fluoro), including mixtures of alkoxy and halo groups. The hydrolyzable aryl silane may therefore have one, two, or three hydrolyzable groups, preferably three hydrolyzable groups which may be the same or different, most preferably the same.

Likewise, the hydrolyzable aryl silane employed may have one, two, or three aryl groups, preferably one aryl group. In cases where the hydrolyzable aryl silane contains one aryl group, the hydrolyzable aryl silane may optionally include one or two alkyl or vinyl substituents bonded directly to the Si atom. The term "aryl", as used herein, and unless otherwise specified, refers to an aromatic group containing carbon in the aromatic ring(s), such as phenyl, biphenyl, naphthyl, anthracenyl, and the like, as well as optionally substituted analogs thereof. The term aryl is also meant to include "heteroaryl" groups, or aryl substituents where at least one carbon atom is replaced with a heteroatom (e.g. nitrogen, oxygen, sulfur) so long as the heteroatom is non-nucleophilic so as to prevent reaction with the hydrolyzable group of a neighboring hydrolyzable aryl silane. Such heteroaryl groups may include, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thia-diazolyl, isothiazolyl, purinyl, carbazolyl, benzimidazolyl, indolinyl, benzodioxolanyl, benzodioxane, and the like, as well as optionally substituted analogs thereof. The nitrogen and sulfur heteroatoms may optionally be oxidized (i.e., N→O and S(O)p, wherein p is 0, 1 or 2) or optionally protected with protecting groups as necessary as known to those skilled in the art, for example, as taught in Greene, et al., "Protective Groups in Organic Synthesis", John Wiley and Sons, Second Edition, 1991, hereby incorporated by reference in its entirety. The term "substituted" refers to at least one hydrogen atom that is replaced with a non-hydrogen group, provided that normal valencies are maintained and that the substitution results in a stable compound. When a compound is noted as "optionally substituted", the substituents are selected from the exemplary group including, but not limited to, alkyl, cycloalkyl, cycloalkylalkyl, arylalkyl, heteroaryl, aryl, heterocyclyl, alkoxy, cycloalkyloxy, aryloxy, arylalkyloxy, aroyl, alkanoyl, alkanoyloxy, carboxy, alkoxycarbonyl, halo (e.g. chlorine, bromine, fluorine or iodine), dialkylamino, diarylamino, arylalkylamino, alkanoylamino, nitro, cyano, carbamyl, alkylthio, arylthio, arylalkylthio, alkylsulfonyl (i.e. —SO$_2$alkyl), arylsulfonyl (i.e. —SO$_2$aryl), arylalkylsulfonyl (i.e. —SO$_2$arylalkyl), haloalkyl, oxo, and the like.

Exemplary hydrolyzable aryl silanes include, but are not limited to, ethoxy(diphenyl)vinyl silane, trichloro[4-(chloromethyl)phenyl] silane, dimethoxy(diphenyl) silane, diethoxy(diphenyl) silane, diethoxy(methyl)phenyl silane, trichloro(phenyl) silane, triethoxy(phenyl) silane, and trimethoxy(phenyl) silane.

In preferred embodiments, the hydrolyzable aryl silane is a trialkoxy(aryl) silane, more preferably a trialkoxy(phenyl) silane, most preferably trimethoxy(phenyl) silane.

It is also envisioned that hydrolyzable arylalkyl silanes may be used in addition to, or in lieu of the hydrolyzable aryl silane, whereby the aryl group is present but is bonded to the Si atom through an alkylene linking group. For example, trimethoxy(2-phenylethyl) silane may be used.

In preferred embodiments, the hydrolyzable aryl silane is the only source, reagent, or starting material used in the present disclosure to synthesize the hollow silica spheres that contains aryl functionality. In preferred embodiments, the hydrolyzable aryl silane is the only Si source utilized in the present method, and other sources of Si, for example tetraethyl orthosilicate (TEOS), may be optionally excluded.

Hydrolysis. Hydrolysis may be carried out by dissolving the hydrolyzable aryl silane in the aqueous solution comprising, consisting essentially of, or consisting of water and an acid with optional stirring and/or heating, for example, heating to a temperature of 30-100° C., preferably 40-90° C., preferably 50-80° C., preferably 55-65° C., preferably 60° C. The amount of the hydrolyzable aryl silane dissolved in the aqueous solution may be varied, although typically a volume ratio of the hydrolyzable aryl silane to the volume of the aqueous solution ranges from 1:50 to 1:100, preferably 1:60 to 1:95, preferably 1:70 to 1:90, preferably 1:75 to 1:85. The water may be tap water, distilled water, twice distilled water, deionized water, deionized distilled water, reverse osmosis water, or various other water sources.

The acid employed in the hydrolysis reaction is preferably a mineral acid such as hydrochloric acid, nitric acid, phosphoric acid, sulfuric acid, hydrobromic acid, perchloric acid, and hydroiodic acid. In preferred embodiments, the acid is nitric acid. A concentration of the acid in the aqueous solution may vary widely, but typical concentrations range from 1-15 mM, preferably 2-13 mM, preferably 3-11 mM, preferably 4-10 mM, preferably 5-9 mM, preferably 6-8 mM.

After combining the hydrolyzable aryl silane with the aqueous solution, the hydrolysis reaction is allowed to take place for an appropriate time to convert the hydrolyzable aryl silane into a partially or fully hydrolyzed form, whereby the hydrolyzable group (e.g., methoxy, chloro, etc.) is replaced by —OH, to form a hydrolyzed silane solution. In most cases, especially when heating is employed, less than 10 minutes, preferably less than 5 minutes, more preferably less than 3 minutes is enough to result in complete hydrolysis, although longer hydrolysis times may also be employed.

In some embodiments, metal oxides or metal salts, such as $Fe_3O_4$ or $\gamma\text{-}Fe_2O_3$ may be incorporated into a mixture to be hydrolyzed, for example, to form Fe-HSS. Nickel and cobalt are also magnetic materials but are toxic. Magnetic cobalt or nickel nanoparticles may be incorporated into HSS by methods similar to those described for $Fe_3O_4$ herein using Co and Ni substrates similar to $Fe_3O_4$, for example, by admixture of their oxides (e.g., $Co_3O_4$ or NiO) or salts with HSS substrates and subsequent hydrolyzation and precipitation. The resulting Co-HSS or Ni-HSS may be used in amounts that minimize toxicity or for applications in which toxicity is not a concern.

Once hydrolysis is deemed sufficiently complete, the hydrolyzed silane solution may be mixed with an appropriate hydroxide base to condense the hydrolyzed silane thereby forming a precipitate.

Hydroxide base. The hydroxide base employed in the condensation reaction may be an alkali metal hydroxide (e.g., lithium hydroxide, sodium hydroxide, potassium hydroxide, rubidium hydroxide, and cesium hydroxide), an alkali earth metal hydroxide (e.g., magnesium hydroxide, calcium hydroxide, strontium hydroxide, and barium hydroxide), or an ammonium hydroxide (e.g., ammonium hydroxide, tetramethylammonium hydroxide, triethylammonium hydroxide, trimethylanilinium hydroxide, etc.). In preferred embodiments, the hydroxide base is ammonium hydroxide.

The hydroxide base may be used in the form of a solid such as a powder, beads or pellets, or may be used in the form of an aqueous base solution. When used as a solid, the hydroxide base is preferably in the form of beads or pellets, more preferably in the form of beads, and still more preferably in the form of beads having an average bead diameter of about 0.1 to 2 mm, preferably about 0.2 to 1.5 mm, more preferably about 0.5 to 1 mm. When the hydroxide base is used in the form of an aqueous base solution, the concentration thereof is preferably about 10 to 50%, preferably about 20 to 40%, more preferably about 30 to 35%, most preferably about 33%, by weight of hydroxide base per total volume of the aqueous base solution.

In some embodiments, an excess of hydroxide base is combined with the hydrolyzed silane solution. For example, a molar ratio of hydroxide base employed in the condensation reaction to the acid employed in the hydrolysis reaction may be about 100:1 to 1000:1, preferably 200:1 to 900:1, preferably 300:1 to 800:1, preferably 400:1 to 700:1, preferably about 500:1. Upon addition of the hydroxide base, a precipitate generally forms immediately at ambient temperatures (i.e., 20-25° C.), or alternatively upon optional heating to 30-80° C., or 40-70° C., or 50-60° C. The resulting suspension may be allowed to settle, or alternatively may be stirred, for example with a mechanical or magnetic stirrer.

Washing Precipitates. The precipitate may then be separated from the suspension, for example by filtration, centrifugation, decantation, and the like, and optionally washed with an organic solvent, water, or both. Exemplary organic solvents may include, but are not limited to $C_1$ to $C_4$ lower alkanols, for example, methanol, ethanol, isopropanol, butanol; polyols and polyol ethers, for example, glycol, 1,3-propanediol, 1,3-butanediol, 2-butoxyethanol, propylene glycol, diethylene glycol, ethylene glycol monomethyl ether, and propylene glycol monomethyl ether. Afterwards, the precipitate may then be dried at a temperature of 20-150° C., preferably 50-120° C., preferably 60-100° C., preferably 80-90° C. under standard pressure or under vacuum. For examples of similar hydrolysis/condensation procedures, see B. P. M. Marini, F. Pilati, and P. Fabbri, *Colloids Surf,* 2008, A 317, (1-3); Y. Taniguchi, K. Shirai, H. Saitoh, T. Yamauchi and N. Tsubokawa, Polymer, 2005, 46, 2541-2547—each incorporated herein by reference in its entirety.

Calcination. Typically calcination is performed at a temperature that removes from the surface of HSS at least 1, 2, 5, 10, 20, 30, 40, 50, 60, 70, 80, 90, 95, 99 or 100% of phenyl or other aryl groups from HSS produced by the methods described herein. Calcination may be used to tune the pharmacological properties of an HSS by selectively removing some or all of the phenyl or other aryl groups on the surface of an HSS.

In some embodiments, the calcining step removes most or preferably all aryl groups that originate from the hydrolyzable aryl silane, from the hollow silica spheres. FTIR can be used to determine the presence/absence of such aryl groups in the hollow silica spheres. The presence of aryl C—H asymmetrical stretching vibration peak at about 3100 $cm^{-1}$ indicates the presence of aryl groups prior to calcination, while the absence of this peak after the calcining procedures described herein indicates removal of at least 90%, preferably at least 95%, preferably at least 99% by weight of the aryl groups.

The method may next involve calcining the precipitate using a multi-stage calcining procedure, preferably a two-stage calcining procedure, to form the hollow silica spheres with advantageous properties as will be discussed hereinafter. In some embodiments, the calcination step is performed in a furnace using, for example, a pre-set temperature program discussed below, or using other variable temperature systems known by those of ordinary skill in the art.

In a first stage of the calcining process, the precipitate may be heated to a first temperature of 180 to 240° C., preferably 185 to 230° C., preferably 190 to 220° C., preferably 195 to 210° C., preferably about 200° C., with a first ramp rate of 3 to 10° C./min, preferably 3.4 to 9° C./min, preferably 3.6 to 8° C./min, preferably 3.8 to 7° C./min, preferably 4 to 6° C./min, most preferably about 5° C./min. Once the first temperature is reached, the first temperature may be held for 2 minutes to 2 hours, preferably from 10 minutes to 1.5 hours, preferably from 12 minutes to 1 hour, preferably from 14 to 55 minutes, preferably from 15 to 45 minutes, preferably from 20 to 40 minutes, preferably from 25 to 35 minutes, preferably about 30 minutes.

After holding the first temperature, the second stage of the calcining process may involve heating to a second temperature of 600 to 740° C., preferably 610 to 730° C., preferably 620 to 720° C., preferably 630 to 700° C., preferably 640 to 680° C., preferably 650 to 670° C., preferably about 660° C., with a second ramp rate of 0.1 to 4° C./min, preferably 0.3 to 3.5° C./min, preferably 0.5 to 3° C./min, preferably 0.8 to 2.5° C./min, preferably 1 to 2° C./min, most preferably about 1.5° C./min. Once the second temperature is reached, the second temperature may be held for 2 to 24 hours, preferably 4 to 23 hours, preferably 6 to 22 hours, preferably 8 to 21 hours, preferably 12 to 20 hours, preferably 14 to 18 hours, preferably 15 to 17 hours, most preferably about 16 hours to form the hollow silica spheres of the present disclosure.

In some embodiments, other stages may be incorporated into the multi-stage calcining program. For example, a third stage may be added in between the first and the second stage that holds on a third temperature which is between the first and second temperatures (i.e., an intermediate stage). Likewise, a fourth stage may be added after the second stage to hold at a fourth temperature that is higher than that of the second temperature to finish the calcining program (i.e., a finishing stage). Various other stages may also be included, as well as other variations known for calcination processes, such as changes of gaseous atmosphere may be practiced.

Ramping. In regard to calcination temperatures and procedures, the term "ramp" or "ramping" refers to a nonisothermal state where the temperature is varied in a particular direction (e.g., increased or decreased) over time, the purpose of which is to move from one temperature setting to another. On the other hand, the terms "held" or "holding" herein refer to an isothermal state where the referenced temperature (e.g., the first temperature or the second temperature) is maintained at a constant or near constant value (i.e., plus or minus 5° C., preferably plus or minus 4° C., preferably plus or minus 3° C., preferably plus or minus 2° C., preferably plus or minus 1° C.) for a certain period of time. For example, when the first temperature is selected to be 200° C., holding this first temperature for 25 to 35 minutes means that the temperature is maintained at 200° C. plus/minus 5° C. for a 25 to 35 minute time period before the temperature is subsequently changed. Therefore, the terms "held" or "holding" distinguish from nonisothermal states (i.e., during periods of temperature ramping) where the temperature is being raised or lowered at a particular ramping rate range. Again using the above example, when the temperature is being ramped from 150° C. to a target temperature of 250° C. over a certain time period, this scenario would not constitute a "hold" in temperature even though 200° C. may be transiently achieved in moving from 150° C. up to 250° C.

As will become clear, the methods disclosed herein provide hollow silica spheres having unexpected and superior monodispersity, uniformity, degree of hollowness, mechanical properties, aqueous solubility, and surface characteristics compared to those produced without calcination and those produced using a single-stage calcination program. In alternative embodiments, other calcining protocols may be used to remove phenyl or other aryl groups from the surface of a HSS and thus increase their antineoplastic properties.

Further, the methods described herein do not require the use of a template for forming the hollow spherical particles, and may thus be considered "template-free" method thus it is not required to employ and subsequently dispose of a sacrificial core used by other methods for making HSS.

The synthesized hollow silica spheres may be used "as is", or may be further functionalized to suit a particular application, for example, for use in slow release or pH-responsive drug delivery applications or other carrier applications, biosensors, catalysis, cosmetics, adsorbent applications, fillers in polymer, building, or construction applications, etc. Indeed, the hollow silica spheres may be surface modified by coating/grafting with poly(N,N-dimethylaminoethyl methacrylate) (PDMAEMA), bi-reactive silanes such as gyycidyl-contianing silanes, e.g., (3-glycidyloxypropyl) trimethoxysilane (GTPMS), cationic polysaccharides such as chitosan or various other coatings known by those or ordinary skill in the art.

"Subject" and "patient" as used herein interchangeably refers to any vertebrate, including, but not limited to, a mammal; e.g., human, non-human primate, cow, pig, camel, llama, horse, goat, rabbit, sheep, hamsters, guinea pig, cat, dog, rat, and mouse. The subject may be a human or a non-human. The subject or patient may have undergone or be undergoing other forms of treatment, for example surgical reduction of a neoplasm, radiological or chemotherapeutic treatment. A subject may be male or female, young or old, for example, <1, 1, 2, 3, 4, 5, 10, 15, 20, 25, 30, 35, 40, 45, 50, 55, 60, 65, 70, 75, 80, 85, 90, 95, 100 or >100 years old or any intermediate value within this range.

In typically embodiments, the subject will have a neoplasm, such as cancer, precancer, or a benign neoplasm. A neoplasm is a type of abnormal and excessive tissue growth called neoplasia. The growth of a neoplasm is typically uncoordinated with that of the normal surrounding tissue and it persists growing abnormally, even if the original trigger is removed. This abnormal growth usually but not always forms a mass which is typically called a tumor. ICD-10 classifies neoplasms into four main groups: benign neoplasms, in situ neoplasms, malignant neoplasms, and neoplasms of uncertain or unknown behavior Malignant neoplasms are also simply known as cancers and are the focus of oncology. Examples of such subjects include those with colon or colorectal cancer, non-melanoma skin cancer, breast cancer, lung cancer, prostate cancer, melanoma, bladder cancer, non-Hodgkin's lymphoma, kidney cancer, leukemia, pancreatic cancer, thyroid cancer, liver cancer, endometrial cancer, throat cancer, ovarian cancer, or testicular cancer.

Subjects having benign neoplasms or pre-cancerous tumors may also be selected for treatment. Benign neoplasms include skin moles, skin tags (acrochordons), cysts in sebaceous glands (sweat glands), breast cysts, encapsulated skin growths such as those triggered by an insect bite or infection, raised scar tissue including keloids, and uterine fibroids.

Modes of Administration. The terms "administration" or "administering" as used herein describes a process by which the disclosed HSS compositions can be delivered to a subject. Administration will often depend upon the amount of composition administered, the number of doses, and duration of treatment. Multiple doses of the composition may be administered. The frequency and duration of administration of the composition can vary, depending on any of a variety of factors, including patient response. The exosome compositions may be administered to the subject by any suitable route. For example, the compositions may be administered parenterally, e.g., by intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, or epidural injection, by infusion, by electroporation, or by co-administration as a component of any medical device or object to be inserted (temporarily or permanently) into a subject. For example, the exosome compositions may be administered intranasally.

The HSS of the invention may be administered by any route that brings them into contact with target neoplastic cells. HSS may be administered systemically, for example, intravenously, or regionally, for example, into an artery that leads to body location containing a tumor. Typically, the HSS are administered parenterally or in in situ to the site of a tumor or cancer cells, though other modes of administration may be selected depending on the type and location of the neoplasm. In some embodiments of the invention HSS are injected directly into neoplasm or tissue or organ containing neoplastic cells.

A "therapeutically effective amount," or "effective dosage" or "effective amount" as used interchangeably herein unless otherwise defined, means a dosage of HSS or other drug or active ingredient effective for periods of time necessary, to achieve the desired therapeutic result such regression of a tumor or other neoplasm. A suitable single dose size is a dose that is capable of inducing or sustaining regression or destruction of a neoplasm in a subject when administered one or more times over a suitable time period. An effective dosage may be determined by a person skilled in the art and may vary according to factors such as the disease state, age, sex, and weight of the individual, and the ability of the drug to elicit a desired response in the individual. Therapeutically effective amounts for the disclosed HSS compositions can be readily determined by those of ordinary skill in the art. A therapeutically effective amount may be administered in one or more administrations. A HSS composition may be given as a preventative treatment or therapeutically at any stage of neoplastic growth. The applications and dosages for an HSS composition are not limited to a particular formulation, combination or administration route. The times of administration and dosages used will depend on several factors, such as the neoplastic disease state, age, sex, and weight of the individual, and the ability of the composition to elicit a desired response in the individual. Administration may be adjusted according to individual need and professional judgment of a person administrating or supervising the administration of the HSS compositions of the present invention.

Any dosage of the HSS as disclosed herein that is effective to inhibit neoplastic growth or induce cytotoxicity may be used. A dosage containing <0.01, 0.01, 0.02, 0.05, 0.1, 0.2, 0.5, 1, 2, 5, 10, 10, 20, 30, 40, 50, 60, 70, 80, 90, 100, 200, 300, 400, 500, 600, 700, 800, 900, 1,000, 2,000, 3,000 or >3,000 µg of HSS per kilogram of body weight of a subject can be used. This range includes all intermediate values and subranges. Dosages may be modified based on mode of administration, for example, a larger dosage may be administered intravenously than a dosage administered in situ to a neoplasm or to a dosage administered topically.

Administration of HSS or HSS loaded with other active ingredients may be as a single dose or multiple doses over a period of time. An HSS composition may be administered to the patient at any frequency necessary to achieve the desired therapeutic effect. For example, it may be administered continuously, once to several times every month, every two weeks, every week, or every day. Administration of an HSS composition may be repeated until the desired therapeutic effect has been achieved. For example, an HSS composition may be administered once to several times over the course of 1 day, 3 days, 5 days, 1, 2, or 3 weeks, or 1, 2, 3, 4, 5, 6, 7, 8, 9, 10, 11 or 12 months or more than 12 months. In some embodiments, compositions containing HSS may be administered before surgery to shrink a tumor or after surgery as an adjuvant chemo therapy.

An amount of HSS in a therapeutic composition to be administered may depend on a variety of factors, such as the route of administration and the seriousness of the condition, and should be decided according to the judgment of the practitioner and each patient's circumstances. An HSS composition may be administered to a subject in any amount suitable for the prevention or treatment of a neoplasm, including cancers or tumors. An effective amount of an HSS composition may partial or complete necrosis or apoptosis of cancer cells, a reduction in tumor size or cancer load, increased cytotoxicity, or a reduction in cancer cell growth rate.

Suitable dosage ranges for the kinds of HSS disclosed herein include from about 0.001 µg HSS/kg body weight to about 100 mg/kg, about 0.01 µg/kg to about 90 mg/kg, about 0.1 µg/kg to about 80 mg/kg, about 1 µg/kg about 70 mg/kg, about 10 g/kg to about 60 mg/kg, about 0.1 mg/kg to about 50 mg/kg, about 0.5 mg/kg to about 25 mg/kg, about 1 mg/kg to about 10 mg/kg, or about 2.5 mg/kg to about 5 mg/kg. For example, suitable dosage ranges of HSS include about 0.001 µg/kg, about 0.01 µg/kg, about 0.1 µg/k, about 1 µg/kg, about 10 µg/kg, about 0.1 mg/kg, about 0.5 mg/kg, about 1 mg/kg, about 2.5 mg/kg, about 5 mg/kg, about 10 mg/kg, about 15 mg/kg, about 20 mg/kg, about 25 mg/kg, about 30 mg/kg, about 40 mg/kg, about 50 mg/kg, about 60 mg/kg, about 70 mg/kg, about 80 mg/kg, about 90 mg/kg, or about 100 mg/kg. In vitro or in vivo assays may optionally be employed to help identify optimal dosage ranges. Effective doses may be extrapolated from dose-response curves derived from in vitro or animal model test systems.

Combination therapy. Anticancer agents that may be administered using HSS or may be coadministered with HSS include 5-flurouracil, capcitbaine, irinotecan, oxaliplatin, trifluridine and tipiracil (Lonsurf) or combinations thereof which are often used to treat colorectal cancer. In a combination therapy the dosage of one or more of the active agents may be reduced thus reducing side-effects associated with a larger dosage. For example, side-effects such as hair loss, mouth sores, loss of appetite, nausea and vomiting, increased risk of infection, easy bruising, fatigue, hand-foot syndrome, neuropathy, allergic or sensitivity reactions, and diarrhea associated with therapy with one or more conventional drugs used to treat colorectal cancer or other kinds of cancer may be reduced by co-administration of HSS with lower dosages of the conventional drugs such as those named above.

HSS conjugates or platforms. HSS may incorporate or be coated with targeting moieties such as antibodies or other that bind to cancer cell antigens. Targeting antibodies or antibody fragments containing an antigen binding site include those that bind to CEA which is associated for example with colon cancer or those that bind to alpha fetoprotein (e.g., liver and testicular cancer), CA15.3 (e.g., breast cancer), CA 19.9 (e.g., gastric/pancreatic cancer), CA125 (e.g., reproductive system cancers), or EVP (e.g., nasopharyngeal cancer).

Fe-HSS may be used in applications where magnetic responsiveness or detection is required, such as the magnetic localization of administered Fe-HSS or drug-loaded Fe-HSS to a particular part of the body. Fe-HSS may also be used in a variety of bioimaging applications.

Other applications of the HSS disclosed herein include their use as nanoparticle collectors, catalysis, and the adsorption and separation of gas and pollutants. For example, they, may be incorporated into a system for adsorption or separation of a liquid or gaseous mixture, as a platform for a catalyst, as thermal or electrical insulators, as a membrane component, as a component of a superhydrophobic surface.

Having generally described this disclosure, a further understanding can be obtained by reference to certain specific examples which are provided herein for purposes of illustration only and are not intended to be limiting unless otherwise specified. The examples below are intended to further illustrate protocols for preparing and testing the hollow silica spheres and they are not intended to limit the scope of the claims.

EXAMPLES

Materials. Phenyltrimethoxysilane (PTMS), ammonium hydroxide ($NH_4OH$), and nitric acid ($HNO_3$) were obtained from Sigma-Aldrich, Inc. Iron oxide ($Fe_3O_4$) nano-powder was supplied from US Research Nanomaterials, Inc. Ultrapure water was produced using a Milli-Q water purification system (Bedford, USA).

The synthesized products were labelled as, uncalcined hollow silica spheres (u-HSS), calcined hollow silica spheres (c-HSS) and iron oxide nanoparticles ($Fe_3O_4$) incorporated hollow silica spheres (Fe-HSS). The scheme of the preparation reaction of Fe-HSS is shown in FIG. 1.

Preparation of uncalcined hollow silica spheres (u-HSS). The hollow silica spheres (HSS) were synthesized substantially as described by Akhtar et al., J. Saudi Chem. Soc., A novel approach to produce monodisperse hollow pure silica spheres (available online Sep. 22, 2018; incorporated by reference).

Briefly, PTMS was dissolved in $HNO_3$ and stirred in an isothermal water bath at 60° C. A solution of $NH_4OH$ was then added which triggered a condensation reaction. Correspondingly, at the adjacency of the PTMS/water interface, the hydrolysis reaction progressed quickly within 3 minutes of the initial acidic condition. The clear mixture rapidly transformed to white colour solution. Precipitated particles were removed from the condensed solution by centrifugation and then washed with ethanol and subsequently with water. The product was dried at 70° C. and labelled as u-HSS.

Preparation of calcined hollow silica spheres (c-HSS). Approximately 100 mg of the synthesized u-HSS were taken and kept in a furnace at the temperature 200° C. for 30 min. Calcination of the u-HSs was performed at 660° C. for 16 hrs. The first and second temperature ramping rates were 5 and 1.5° C./min, respectively. The calcined product was labelled as c-HSS and is shown in FIG. 2A.

Preparation of magnetic nanoparticles doped HSS (Fe-HSS). Magnetic nanoparticle-doped HSS were produced by introducing 60 mg of iron oxide ($Fe_3O_4$) powder into 50 ml of 6.6 mM $HNO_3$ solution in a 3-neck round bottom flask which was shaken for 10 minutes.

Then 0.6 ml PTMS was added into the solution and the mixture was again shaken for 10 minutes.

The resulting mixture was then placed into water bath at 60° C. Then 8.5 ml of a $NH_4OH$ solution (33%) was added producing a milky solution which was kept in the water bath for 1 hour. The water bath was allowed to cool to room temperature and the mixture was then removed. The final mixture was stirred for about 16 hours at room temperature.

Precipitated particles were recovered from the condensed solution by centrifugation. The precipitated particles were initially washed with ethanol and then with water and the product was dried at 70° C. and labelled as Fe-HSS as shown by FIG. 5B.

Characterization of HSS. The sizes and structures of the $Fe_3O_4$ nanoparticles were analyzed by Transmission Electron Microscopy (TEM) (Model:FEI, Morgagni 268, Czech Republic). The morphological features of the u-HSS, c-HSS and Fe-HSS were also examined by TEM. For that purpose, a droplet of suspension of either HSS or Fe-HSS was deposited onto TEM grid supported by carbon support film. TEM was operated at accelerating voltage of 80 kV. Several images were taken to obtain the size of the nanoparticles and the Gatan digital micrograph software was applied to measure the size of the particles. More than 250 individual $Fe_3O_4$-particles were measured to obtain a size histogram. The crystalline structure of the nanoparticles was verified by selected area electron diffraction (SAED) pattern. Furthermore, the overall morphology of u-HSS, c-HSS and Fe-HSS products were examined by Scanning Electron Microscopy (SEM) (Model: FEI, Inspect S50, Czech Republic) where SEM was operated at 20 kV as shown by FIGS. 1D-1F.

X-ray diffraction (XRD) of Fe-HSS specimen was performed to confirm the existence of $Fe_3O_4$ in the silica spheres. An XRD pattern was taken by an X-ray Diffractometer obtained from Rigaku, Japan by using Cu-K$\alpha$ radiations ($\lambda$=0.154 nm) within the 2$\theta$ range of 15°-70°. The XRD instrument was operated at 40 kV and 15 mA.

Thermal stability. The thermal stability of u-HSS, c-HSS and Fe-HSS were examined by Thermogravimetric analysis (TGA) and the analysis was carried out using a thermal analyzer (STA, Parkin-Elmer) 6000, USA. TGA data of samples were obtained between temperatures ranging from 25 to 700° C. with a heating rate of 10° C./min under a nitrogen atmosphere. Nitrogen flow rate was maintained at 20 ml/min.

Treatment of cancer cells with c-HSS, u-HSS2, and Fe-HSS. Human colorectal carcinoma (HCT-116) cells were grown as previously described by Khan F A, Akhtar S, Almohazey D, Alomari M, Almofty S A, Eliassari A. Fluorescent magnetic submicronic polymer (FMSP) nanoparticles induce cell death in human colorectal carcinoma cells. Artif Cells Nanomed Biotechnol. 2018 Jul. 25:1-7. doi: 10.1080/21691401.2018.1491476. In brief, HCT-116 cells were grown in DMEM, supplemented with 10% fetal bovine serum, L-glutamine, selenium chloride, penicillin, and streptomycin. The cells were seeded in 96 well plates and grown to 80% confluence in a $CO_2$ incubator (Thermo-scientific, Waltham, MA, USA) in an atmosphere containing 5% $CO_2$ at 37° C. Then, the cells were treated with c-HSS, u-HSS, or Fe-HSS each at the following concentrations 1 mg/mL, 3 mg/mL, 5 mg/mL, and 7 mg/mL respectively. After 48 hours, the cells were microscopically observed. Triplicate samples for each grouping were prepared for statistical evaluation.

Cancer Cell Morphology. After the treatments with c-HSS, u-HSS2, and Fe-HSS, the cancer cells were observed microscope (TS100E-Eclipse, Nikon, Japan) to evaluate the anatomical and morphological changes and each sample was observed under 200 and 400 magnifications respectively.

Cancer cells viability determined by MTT assay. To examine the effects of exposure of cancer cells to c-HSS, u-HSS, and Fe-HSS an MTT assay was performed. The cancer cells were seeded with $6 \times 10^4$ cells/mL concentration in 96-well culture plates containing DMEM, supplemented with 10% Fetal bovine serum, penicillin and streptomycin and were incubated in $CO_2$ incubator till they reached 80% confluence. Then, cancer cells were treated with c-HSS, u-HSS, and Fe-HSS at the following concentrations: 1 mg/mL, 3 mg/mL, 5 mg/mL, and 7 mg/mL respectively. The c-HSS, u-HSS, and Fe-HSS were not added to the control groups.

MTT (5 mg/mL) solution was added and cells were incubated for 4 hrs in the $CO_2$ incubator and finally media was changed with the addition of DMSO. The samples were processed for OD reading using ELISA plate reader (Biotek Instruments, Winooski, USA) at 570 nm wavelength. The percentage (%) of cell viability was calculated as per below given formula:

% of Cell viability=(Optical density (OD) of c-HSS, u-HSS,Fe-HSS-treated cells)/(Optical density (OD) of control cells×100)

Statistical analysis. The mean±standard deviation (SD) from control and c-HSS, u-HSS2, and Fe-HSS treated groups were calculated. All statistical analyses were completed with GraphPad Prism 6 (GraphPad Software). The difference between control and c-HSS, u-HSS, and Fe-HSS groups by a one-way analysis of variance (ANOVA) test where ($P<0.05$) was considered statistically significant.

Morphological and structural analysis. SEM and TEM are widely used to analyze the surface morphology and structure of the nanomaterials at high resolution. FIGS. 2A-2F show the morphological analysis of the $Fe_3O_4$ particles and hollow silica spheres (HSS) synthesized under different conditions. The nano-powder of $Fe_3O_4$ exhibited the spherical-shaped particles with a bit of agglomeration (FIG. 2A). Several particles, more than 250 individual particles were selected from different TEM images and measured.

Figure 2B:
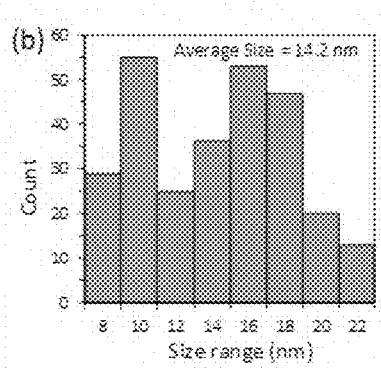

The results of this measurement are drawn in the form of size histogram (FIG. 2B). The average diameter of the particles was found 14.2±1.4 nm.

Figure 2C:
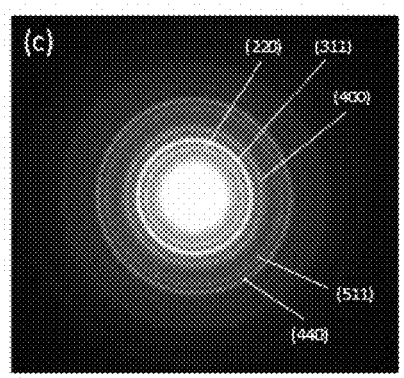

The $Fe_3O_4$ nanoparticles showed the polycrystalline nature when analyzed by selected area electron diffraction (SAED) pattern (FIG. 2C). The first 5-rings of the SAED pattern started from the inner ring are indexed as, (220), (311), (400), (511) and (440), confirming the structure of $Fe_3O_4$ crystal.

Figure 2D:
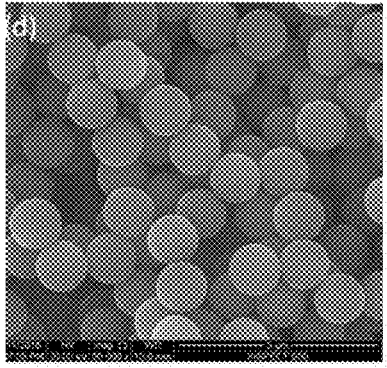
Figure 2E:
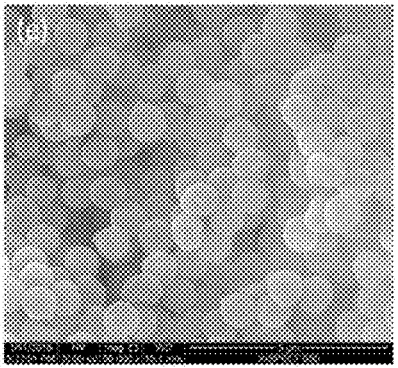
Figure 2F:
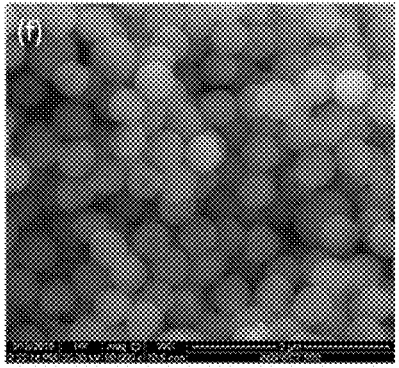

FIGS. 2D-2F show the SEM micrographs of u-HSS, c-HSS and $Fe_3O_4$ doped HSS (Fe-HSS) specimens.

As shown by the TEM analysis, the silica spheres appeared monodispersed and showed well-organized spherical shape having smooth and uniform texture. The size of u-HSS was measured which was found to be around 760 nm (FIG. 2D).

Upon applying the calcination step, the size of c-HSS was reduced substantially (FIG. 2E).

The average diameter of the c-HSS was estimated to be 515±15 nm. A similar size was found for the magnetic nanoparticles incorporated silica specimen (Fe-HSS), see FIG. 2F.

All prepared products, u-HSS, c-HSS and Fe-HSS were further analyzed by TEM (FIG. 3).

Figure 3A:
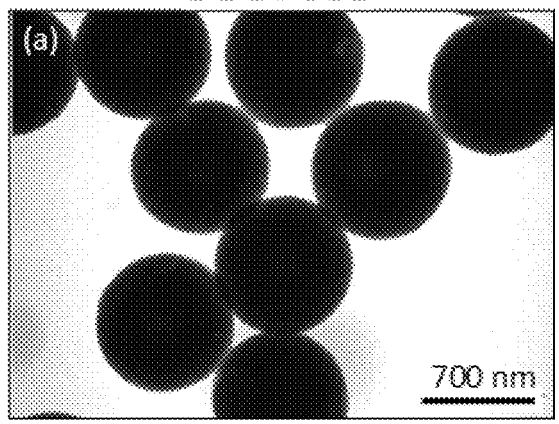
FIGS. 3A-3D. Morphology and size analysis of hollow silica spheres (HSS). TEM image of (FIG. 3A) u-HSS, (FIG. 3B) c-HSS and (FIGS. 3C and 3D) Fe-HSS. A shell and a core are marked in FIG. 3B. The $Fe_3O_4$ nanoparticles inside the HSS are highlighted by white arrows in FIG. 3D.
Figure 3B:
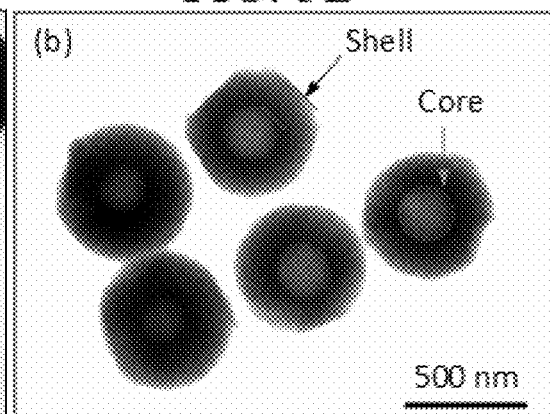

FIG. 3A displayed the morphology of several uncalcined spheres (u-HSS specimen). As analyzed by TEM, the u-HSS were larger in diameter compared to c-HSS and Fe-HSS specimens (see FIGS. 3A-3C). This was expected due to presence of phenyl groups with silica spheres. This result is consistent with the observation made earlier by SEM (see FIG. 3D-3F).

Furthermore, the TEM images resolved the hollow structure of the spheres as evident by the bright contrast in the middle of the spheres. The shells of the spheres are appeared darker compared to hollow cores due to their solid nature. The shell/core structure is more evident and visible for the c-HSS specimen (FIG. 3B), where the brightness of the image is increased a lit bit to clarify the core and shell.

TEM micrographs showed the clear evidence of the core structure of the silica spheres. It was found that the shells were larger in thickness than the size of the cores.

Figure 3C:
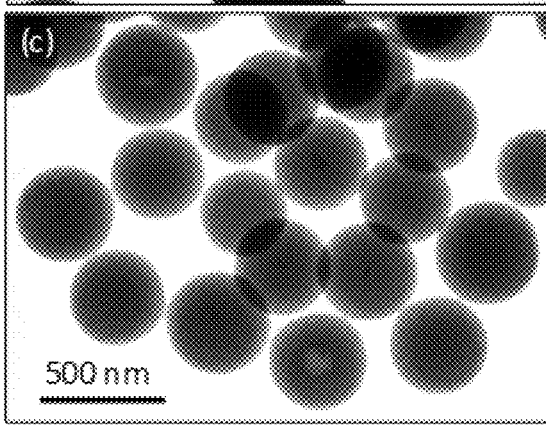
Figure 3D:
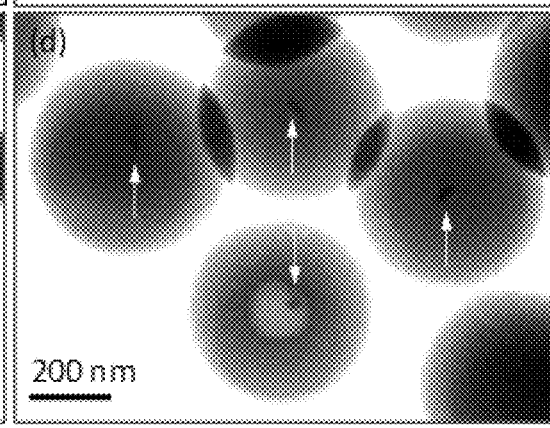

FIGS. 3C and 3D showed the TEM micrographs of Fe-HSS specimen at two magnifications.

Excitingly, the $Fe_3O_4$ nanoparticles were seen in the core of the silica spheres. Few such $Fe_3O_4$ nanoparticles inside the core are highlighted by white arrows in FIG. 3D, identified by their darker contract compared to hollow core.

SEM and TEM analysis confirm the successful loading of $Fe_3O_4$ nanoparticles to hollow silica spheres.

The presence of $Fe_3O_4$ in the HSS product was verified by performing energy dispersive X-Ray specroscopy (EDS). The EDS analysis confirms the presence of iron in the HSS product, where about 5% Fe was found in the Fe-HSS specimen.

Figure 4:
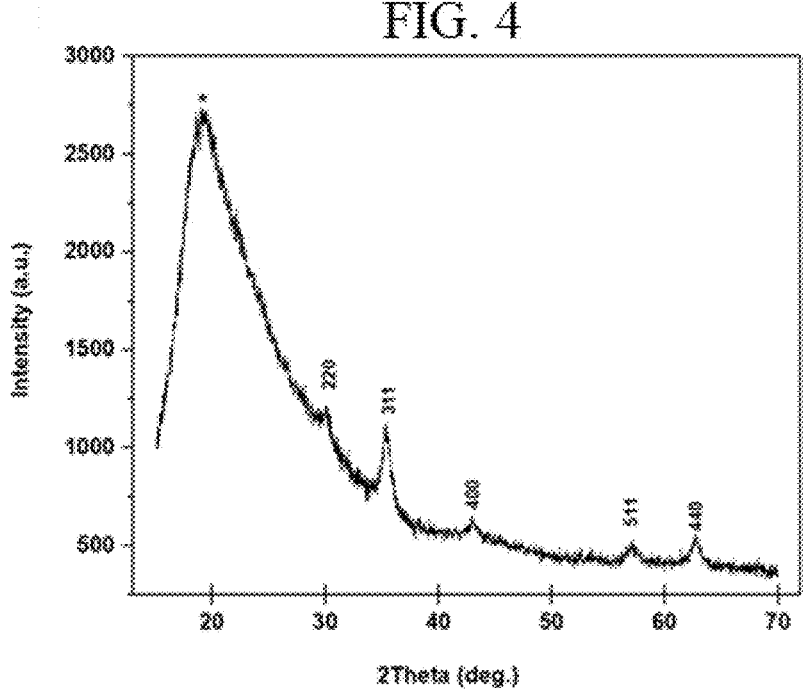
FIG. 4. XRD pattern of Fe-HSS specimen. The main peaks of $Fe_3O_4$ are indexed in the pattern. The broad peak marked with * is related to amorphous silica.

In addition to SEM and TEM, X-Ray diffraction (XRD) analysis was performed on Fe-HSS specimen to confirm the presence of $Fe_3O_4$ nanoparticles in the HSS. FIG. 4 shows the results of XRD powder pattern of Fe-HSS within the 2θ range of 15°-70°. The broad diffraction peak at 20° marked with * symbol is ascribed to the amorphous silica. The XRD patterns of u-HSS showed that silica spheres show the similar pattern. The diffraction peaks of [2 2 0], [3 1 1], [4 0 0], [4 4 0], and [5 1 1] proved the existence of $Fe_3O_4$ spinel structure in the HSS, thus confirming the presence of magnetic nanoparticles within the silica spheres. This result is in good agreement with electron diffraction data shown in FIG. 2C, where $Fe_3O_4$ nanoparticles were analyzed by SAED pattern obtained by TEM. The intense peak/ring in both cases is (311).

The physical appearance of two products, c-HSS and Fe-HSS, is shown by FIGS. 5A and 5B, respectively. The c-HSS specimen showed the white milky colour whereas Fe-HSS powder gave the blackish appearance, indicating the presence of iron oxide in this product.

The presence of $Fe_3O_4$ nanoparticles in Fe-HSS was also confirmed by performing a simple test as shown by FIGS. 5C and 5D. The Fe-HSS powder was pulled by magnetic slab as shown by FIG. 5D, while c-HSS specimen showed no attraction to the magnetic slab.

The Fe-HSS powder attached to magnetic slab can be seen in FIG. 5D, confirming the presence of magnetic nanoparticles in the sample. FIG. 5C shows the same slab without magnetic particles of Fe-HSS attached to it.

TG analysis. Thermo-gravimetric analysis ("TGA") of c-HSS, u-HSS and Fe-HSS is shown in FIG. 6. TGA plots of the various HSS were prepared between the temperature ranging from 25° C. to 750° C. A minor weight loss of HSS between the temperature ranges from 25 to 400° C. was observed. The u-HSS exhibited a single step degradation starting with the temperature 400° C., which is corresponded to the loss of phenyl groups. In addition, we have also observed significant weight loss for u-HSS and magnetic nanoparticles after 550° C. On the other hand, the c-HSS shows no visible weight change and remain constant during 25° C. to 750° C. The results were further explained by TEM analysis in FIG. 2, where a 30% (760 to 510 nm) reduction in the average size of the spheres was observed. This reduction in HSS was caused by loss of phenyl groups after calcination at the temperature of 660° C. The thermal stability of the calcined product is explained in FIG. 6 where the organic-natured phenyl molecules were removed slowly without changing the morphology of HSS. By removing the organic groups from the final product, the thermal stability of HSS was obtained.

Effect of u-HSS on cancer cell morphology. The treatment of u-HSS (uncalcined HSS) with dose 1 mg/mL showed little impact on the cancer (FIG. 7B) with compared to control cells (FIG. 7A). The dose of 4 mg/mL showed moderate nuclear condensation and augmentation of cancer cells (FIG. 7C). Whereas, the dosages of 5 mg/mL and 7 mg/mL showed some changes in cancer cell morphology but not many cell deaths (FIG. 7D).

Effect of c-HSS on cancer cell morphology. Post 48-hour treatment of c-HSS (calcined HSS) with dose 1 mg/mL showed moderate levels of nucleus condensation and nuclear augmentation of the HCT-116 cells (FIG. 8B) with compared to control cells (FIG. 8A). The dose of 3 mg/mL showed strong nuclear condensation and augmentation and showed the beginning of cell membrane disruption (FIG. 8C). The dosages of 5 mg/mL and 7 mg/mL showed a significant loss of cell population (FIG. 8D).

Figure 9A:
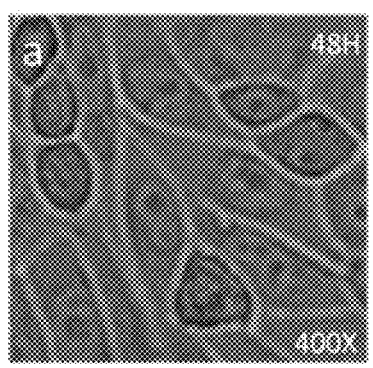
FIGS. 9D and 9E show complete disintegration of cell bodies. 400× magnifications.
Figure 9B:
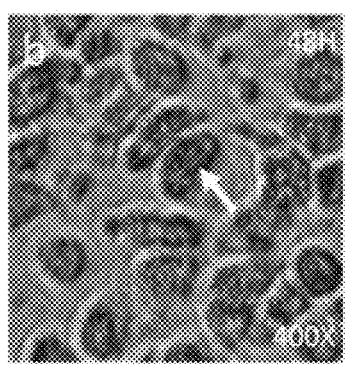
Figure 9C:
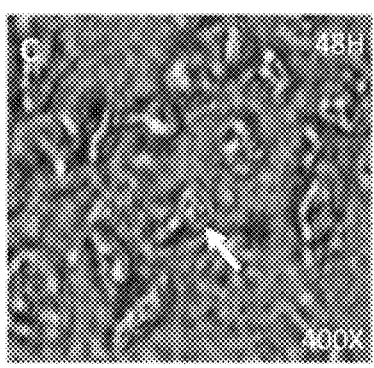
Figure 9D:
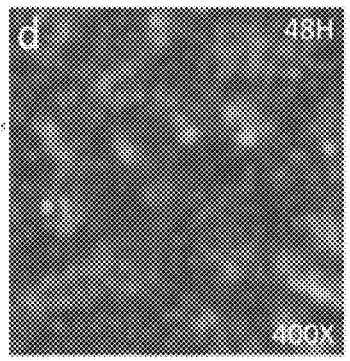
Figure 9E:
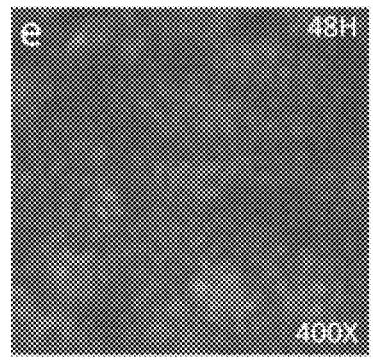

Effect of Fe-HSS on cancer cell morphology. The treatment of cells with Fe-HSS (1 mg/mL) showed strong nucleus condensation and nuclear augmentation of the cancer cells (FIG. 9B). No morphological changes in the control cells (FIG. 9A) were observed. The dose of 3 mg/mL showed further nucleus condensation and augmentation (FIG. 9C), whereas the dosages of 5 mg/mL and 7 mg/mL showed a significant loss of cell population (FIG. 9D).

Figure 10:
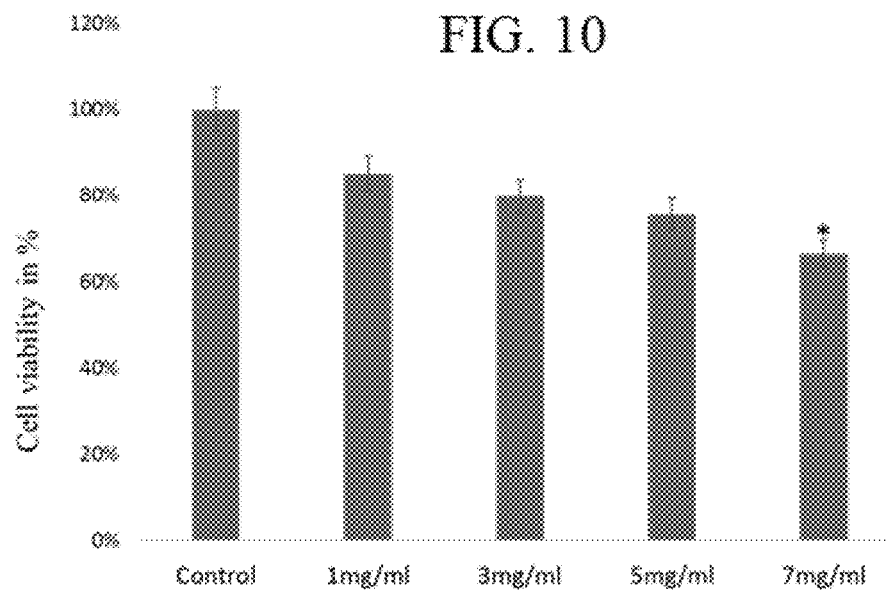
FIG. 10. Cancer cell viability by MTT Assay. The HCT-116 cells were treated with Uncal-HSS (1 mg/mL, 3 mg/mL, 5 mg/mL, 7 mg/mL) for 48 hrs. Data are the means±SD of three different experiments. Difference between two treatment groups were analysed by student's t test where (*$p<0.05$), p-values were calculated by Student's t-test. No changes were observed in control group.
Figure 11:
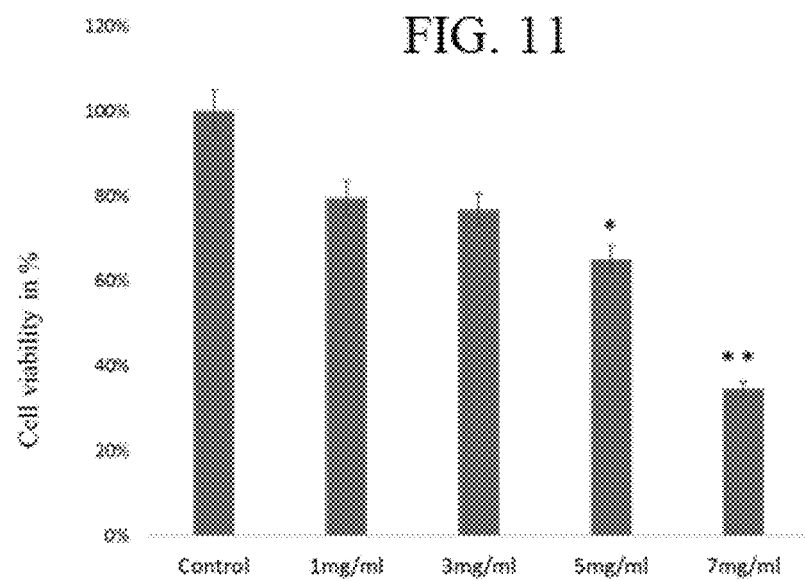
FIG. 11. Cancer cell viability by MTT Assay. The HCT-116 cells were treated with Cal-HSS (1 mg/mL, 3 mg/mL, 5 mg/mL, 7 mg/mL) for 48 hrs. Data are the means±SD of three different experiments. Difference between two treatment groups were analyzed by student's t test where (*$p<0.05$, **$p<0.01$), p-values were calculated by Student's t-test. No changes were observed in control group.
Figure 12:
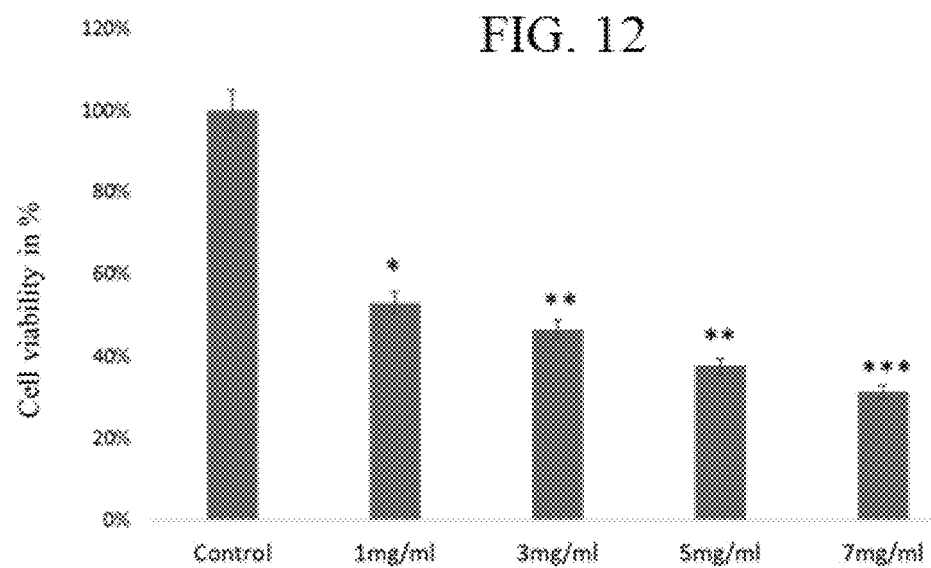
FIG. 12. Cancer cell viability by MTT Assay. The HCT-116 cells were treated with Fe-HSS (1 mg/mL, 3 mg/mL, 5 mg/mL, 7 mg/mL) for 48 hrs. Data show the means±SD of three different experiments. Differences between two treatment groups were analyzed by student's t test where (*$p<0.05$, $p<0.01$; *$p<0.001$), p-values were calculated by Student's t-test. No changes were observed in control group.

Cancer cells survivability. MTT assays were carried out to examine cell viability and the inhibition rate of HCT-116 cell line. MTT assay was carried with different concentrations of u-HSS, c-HSS2, and Fe-HSS for 48 hrs. The treatment using 1 mg/mL, 3 mg/mL, 5 mg/mL, and 7 mg/mL) of u-HSS showed 85%, 79.68%, 75.52, and 66.40% cancer cell viability (FIG. 10), whereas the treatment of c-HSS using 1 mg/mL, 3 mg/mL, 5 mg/mL, and 7 mg/mL showed 79.42%, 76.82%, 65.18%, and 34.56% cell viability respectively (FIG. 11). When cancer cells were treated with Fe-HSS using 1 mg/mL, 3 mg/mL, 5 mg/mL, and 7 mg/mL, the cancer cell viability was significantly reduced to 53%, 46.48%, 37.63% and 31.26% respectively (FIG. 12).

As shown by the work described above, the inventors have synthesized u-HSS, c-HSS, and Fe-HSS and all these HSSs were found to be highly soluble in water. The physical properties of the u-HSS, c-HSS2, and Fe-HSS were characterized. The size and structure and morphological features of the uncalcined (u-HSS), calcined (c-HSS) and $Fe_3O_4$ doped HSS (Fe-HSS) were examined by taking droplet of suspension of either HSS or Fe-HSS onto TEM grid with carbon support film. SEM and TEM are widely used to analyze the surface morphology and structure of the nanomaterials at high resolution. The nano-powder of $Fe_3O_4$ exhibited spherical-shaped particles with a bit of agglomeration, several particles, more than 250 individual particles were selected from different TEM images and measured. The average diameter of the particles was found 14.2±1.4 nm. The $Fe_3O_4$ nanoparticles showed the polycrystalline nature when analyzed by selected area electron diffraction (SAED) pattern. The first 5-rings of the SAED pattern started from the inner ring are indexed as, (220), (311), (400), (511) and (440), confirming the structure of $Fe_3O_4$ crystal as reported by other researchers; Xiong, Z., et al., A facile method for the room-temperature synthesis of water-soluble magnetic $Fe_3O_4$ nanoparticles: Combination of in situ synthesis and decomposition of polymer hydrogel. Materials Chemistry and Physics, 2011. 130(1-2): p. 72-78; Liu et al., 2015. The average size of the u-HSS was measured around 760 nm, which was found to be consistent with the size found by another researcher; Hah, H. J., et al., Simple preparation of monodisperse hollow silica particles without using templates. Chemical Communications, 2003 (14): p. 1712-171.

The XRD patterns of u-HSS and c-HSS were shown in our previous work (Akhtar et al., 2018), where silica spheres showed the similar pattern. The diffraction peaks of [2 2 0], [3 1 1], [4 0 0], [4 4 0], and [5 1 1] proved the existence of $Fe_3O_4$ spinel structure in the HSS (Liu et al., 2017) which confirmed the presence of magnetic nanoparticles within the silica spheres. The thermal stability of the calcined product can be explained by applying a calcination step, where the organic-natured phenyl molecules were removed slowly without changing much the morphology of HSS. The thermal stability of HSS was obtained by the removal of these organic groups from the final product.

After confirming the physical and structural properties of u-HSS, c-HSS, and Fe-HSS, their properties as anti-cancer agents were evaluated. Human colorectal carcinoma cells (HCT-116) were used to evaluate anti-cancer properties of -HSS, c-HSS, and Fe-HSS. HSS were found to produce concentration dependent effects on cancer cells. The microscopic examination of both control and -HSS, c-HSS, and Fe-HSS treated cancer cells showed that u-HSS, c-HSS, and Fe-HSS not only induced nuclear condensation, augmentation and disintegration but also affected the cancer cell membrane. Thus, u-HSS, c-HSS, and Fe-HSS are all highly effective in attenuating cancer cells proliferation, however, the response of c-HSS (calcined HSS) was better than u-HSS (uncalcined HSS) and Fe-HSS was more effective in reducing cancer cell proliferation compared to u-HSS and c-HSS. While not being bound to any theory or explanation, the inventors consider that the absence of phenyl groups in the c-HSS and Fe-HSS makes them more effective in targeting cancer cells and inducing cytotoxicity.

As shown by the above Examples, the inventors synthesized different forms of hollow silica spheres (HSS) with $Fe_3O_4$ (Fe-HSS) and without $Fe_3O_4$ (u-HSS and c-HSS) and tested their anti-cancer aptitudes on the cancer cells. They found that all forms of HSS reduced cancer cells proliferation with dose dependent manner. The lower dosage (1 mg/mL) produced minor effect on the cancer cells proliferation, while the higher dosages (3, 5 and 7 mg/mL) significantly reduced the cancer cell proliferation during the same period (48 hrs). In addition, the inventors have shown that u-HSS, c-HSS and Fe-HSS treated cancer cells undergo nuclear disintegration and fragmentation. The inventors also identified a differential action of u-HSS, c-HSS, and Fe-HSS, for example, Fe-HSS was more effective in reducing cancer cell proliferation compared to u-HSS and c-HSS and u-HSS was less effective than c-HSS. These surprising results indicate the usefulness of hollow silica spheres, particularly those from which phenyl/aryl groups have been removed, or those containing $Fe_3O_4$, are for biological application such as treatment of neoplasms.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

A weight percent of a component, unless specifically stated to the contrary, is based on the total weight of the formulation or composition in which the component is included. For example, if a particular element or component in a composition is said to have 8 wt. %, it is understood that this percentage is in relation to a total compositional percentage of 100%, unless stated otherwise.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for forming hollow silica spheres incorporating $Fe_3O_4$ ("Fe-HSS"), comprising:
    dissolving a hydrolyzable aryl silane comprising phenyl-tri-methoxysilane in an aqueous solution comprising $Fe_3O_4$, water and an acid to form a hydrolyzed silane solution, wherein a molar ratio of the hydrolyzable aryl silane to the $Fe_3O_4$ ranges from 100:1 to 1:100;
    mixing the hydrolyzed silane solution with a hydroxide base to form a precipitate; and
    calcining the precipitate to form the Fe-HSS, wherein the calcining is carried out in two stages including a first stage of heating at a rate of 3.6 to 8° C./min to a first temperature of 185 to 230° C. and holding at the first temperature for about 15 minutes to 45 minutes, and a second stage of heating at a rate of 1° C. to 2° C./min to a second temperature of 600 to 740° C. and holding at the second temperature for about 12 hours to 24 hours;
    wherein surfaces of the Fe-HSS comprise no more than 0.1 mol % phenyl or aryl groups relative to an average uncalcined Fe-HSS,
    wherein the Fe-HSS have a hollow core space containing plural individual particles of $Fe_3O_4$ having an average diameter in a range of from 9.5 nm to 21.3 nm and the $Fe_3O_4$ has a spinel structure,
    wherein the hollow silica spheres of the $Fe_3O_4$ hollow silica spheres have a core-shell structure with shells larger in thickness than cores, and the hollow silica spheres have an average diameter in a range of from 415 to 615 nm,
    wherein the hollow silica spheres of the $Fe O_4$ hollow silica spheres have an average diameter less than the average diameter of the corresponding uncalcined Fe-HSS; and
    wherein the particles of $Fe_3O_4$ are present in an amount of from 0.1 to 10 wt. % of a combined weight of the HSS and $Fe_3O_4$ in the Fe-HSS.

2. The method of claim 1, wherein the hydrolyzable aryl silane is trimethoxy(phenyl) silane and the hydroxide base is $NH_4OH$.

3. The method of claim 1, wherein the Fe-HSS have a BET surface area in a range of from 350 to 450 $m^2/g$.

4. The method of claim 1, wherein the Fe-HSS has an average shell thickness in a range of from 150 to 210 nm.

5. The method of claim 1, wherein the surfaces of the Fe-HSS comprise no more than 0.05 mol. % phenyl or aryl groups, relative to an average uncalcined Fe-HSS.

6. The method of claim 1, wherein the surfaces of the Fe-HSS comprise no more than 0.02 mol. % phenyl or aryl groups, relative to an average uncalcined Fe-HSS.

7. The method of claim 1, wherein the surfaces of the Fe-HSS comprise no more than 0.01 mol. % phenyl or aryl groups, relative to an average uncalcined Fe-HSS.

8. The method of claim 1, further comprising recovering the Fe-HSS.

9. The method of claim 8, wherein the dissolving forms a mixture that consists of the hydrolyzable aryl silane, water, $Fe_3O_4$, the acid and a hydrolyzed silane product.

10. The method of claim 1, wherein the surfaces of the Fe-HSS comprise no phenyl or aryl groups.

* * * * *